US007064837B2

(12) United States Patent
Mori et al.

(10) Patent No.: US 7,064,837 B2
(45) Date of Patent: Jun. 20, 2006

(54) MEASURING SENSOR UTILIZING ATTENUATED TOTAL REFLECTION AND MEASURING CHIP ASSEMBLY

(75) Inventors: Nobufumi Mori, Kaisei-machi (JP); Katsumi Hayashi, Kaisei-machi (JP); Masayuki Naya, Kaisei-machi (JP); Nobuhiko Ogura, Kaisei-machi (JP); Yoshiyuki Kunuki, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 252 days.

(21) Appl. No.: 10/120,518

(22) Filed: Apr. 12, 2002

(65) Prior Publication Data

US 2002/0149775 A1   Oct. 17, 2002

(30) Foreign Application Priority Data

Apr. 12, 2001   (JP)   ............................. 2001-113646

(51) Int. Cl.
*G01N 21/55*   (2006.01)
*G01N 1/10*   (2006.01)

(52) U.S. Cl. ...................................... 356/445; 356/246
(58) Field of Classification Search ................ 356/445, 356/246
See application file for complete search history.

(56) References Cited

U.S. PATENT DOCUMENTS

| 4,810,658 A | * | 3/1989 | Shanks et al. | ............... 436/172 |
| 5,443,791 A | | 8/1995 | Cathcart et al. | |
| 6,143,250 A | * | 11/2000 | Tajima | ........................ 422/102 |
| 6,271,040 B1 | * | 8/2001 | Buechler | ..................... 436/170 |

FOREIGN PATENT DOCUMENTS

| JP | 04-292126 | 10/1992 |
| JP | 04-353747 | 12/1992 |
| JP | 6-167443 | 6/1994 |
| JP | 08-327532 | 12/1996 |
| JP | 10-300667 | 11/1998 |
| JP | 11-064213 | 3/1999 |
| JP | 2000-65729 | 3/2000 |

(Continued)

OTHER PUBLICATIONS

Takayuki Okamoto; "Surface Refracto-Sensor using Evanescent Waves" Spectrum Researches; vol. 47, No. 1, 1998, pp. 21-23, 26-27.

*Primary Examiner*—Gregory J. Toatley, Jr.
*Assistant Examiner*—Amanda Merlino
(74) *Attorney, Agent, or Firm*—Sughrue Mion, PLLC

(57) ABSTRACT

Disclosed herein is a sensor utilizing attenuated total reflection. The sensor is constructed of a measuring chip, an optical system, and a measuring section. The measuring chip is equipped with a dielectric block, a thin film layer formed on the dielectric block, and a liquid-sample holding portion for holding a liquid sample. The optical system is used to make a light beam enter the dielectric block at various angles of incidence so that a total internal reflection condition is satisfied at an interface between the dielectric block and the thin film layer. The measuring section measures the state of attenuated total reflection, based on the intensity of the light beam totally reflected at the interface. The liquid-sample holding portion has an opening at its top surface. The sensor further has a lid supply mechanism for placing a lid on the opening to prevent evaporation of the liquid sample.

19 Claims, 20 Drawing Sheets

FOREIGN PATENT DOCUMENTS

| | | |
|---|---|---|
| JP | 2000-352554 | 12/2000 |
| JP | 1 079 226 A1 | 2/2001 |
| JP | 2001-061464 | 3/2001 |
| WO | WO 95/22754 | 8/1995 |

* cited by examiner

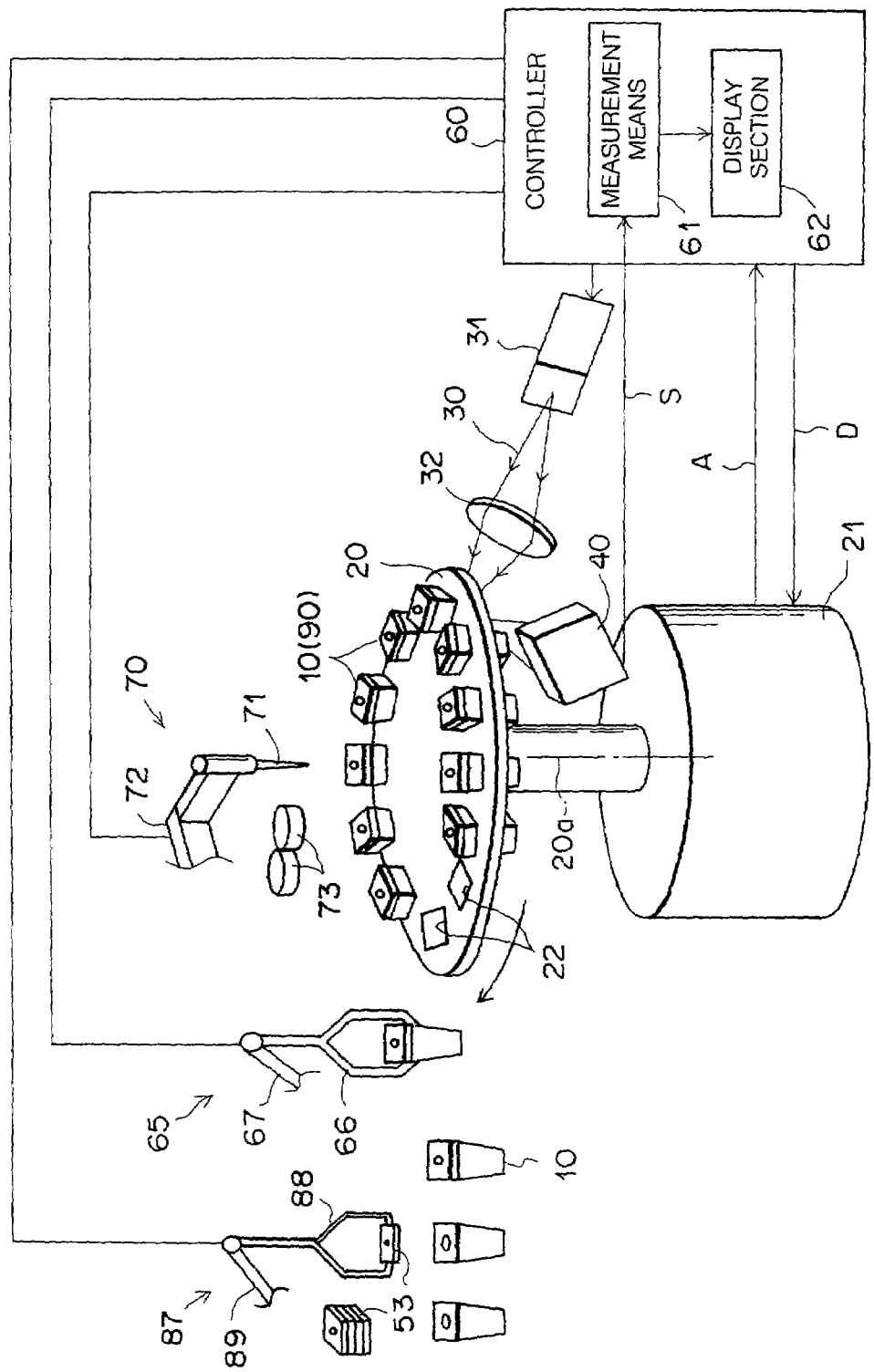

MEASURING SENSOR UTILIZING ATTENUATED TOTAL REFLECTION AND MEASURING CHIP ASSEMBLY

BACKGROUND OF THE INVENTION

1. Field of the Invention

The present invention relates to a sensor and a measuring chip assembly utilizing attenuated total reflection (ATR), such as a surface plasmon resonance sensor for quantitatively analyzing a substance in a liquid sample by utilizing surface plasmon excitation, and more particularly to a sensor and a measuring chip assembly, utilizing ATR, which employ a measuring chip equipped with one or a plurality of liquid-sample holding portions for holding a liquid sample.

2. Description of the Related Art

In metals, if free electrons are caused to vibrate in a group, a compression wave called a plasma wave will be generated. The compression wave, generated in the metal surface and quantized, is called a surface plasmon.

There have hitherto been proposed various kinds of surface plasmon resonance sensors for quantitatively analyzing a substance in a liquid sample by taking advantage of a phenomenon that the surface plasmon is excited by a light wave. Among such sensors, one employing a system called the "Kretschmann configuration" is particularly well known (e.g., see Japanese Unexamined Patent Publication No. 6(1994)-167443).

The surface plasmon resonance sensor employing the aforementioned system is constructed basically of a measuring chip, a light source for emitting a light beam, an optical system, and photodetection means. The measuring chip is equipped with a dielectric block; a thin film layer consisting of a metal film formed on the top surface of the dielectric block; and a liquid-sample holding portion for holding a liquid sample on the thin film layer. The dielectric block is formed, for example, into the shape of a prism. The optical system is used to make the light beam enter the dielectric block at various angles of incidence so that a condition for total internal reflection (TIR) is satisfied at the interface between the dielectric block and the thin film layer. The photodetection means measures the intensity of the light beam totally reflected at the interface, and detects the state of surface plasmon resonance, that is, the state of ATR.

To obtain various angles of incidence in the aforementioned manner, a relatively thin light beam is caused to strike the aforementioned interface at different angles of incidence, or a relatively thick light beam is caused to strike the interface convergently or divergently so that it includes components incident on the interface at various angles of incidence. In the former, the light beam whose reflection angle changes according to changes in the incidence angle thereof can be detected by a photodetector movable in synchronization with the reflection angle changes, or by an area sensor extending along the direction in which the reflection angle changes. In the latter, the light beams reflected at various angles can be detected by an area sensor extending in the direction where all the reflected light beams can be received.

In the surface plasmon resonance sensor mentioned above, if a light beam strikes the thin film layer at a specific incidence angle $\theta_{sp}$ greater than a critical incidence angle at which total internal reflection (TIR) takes place, an evanescent wave having electric field distribution is generated in a liquid sample in contact with the thin film layer. The evanescent wave excites surface plasmon at the interface between the thin film layer and the liquid sample. When the wave vector of the evanescent wave is equal to the wave number of the surface plasmon and therefore the wave numbers between the two are matched, the evanescent wave resonates with the surface plasmon and the light energy is transferred to the surface plasmon, whereby the intensity of the light totally reflected at the interface between the dielectric block and the thin film layer drops sharply. This sharp intensity drop is generally detected as a dark line by the aforementioned photodetection means.

Note that the aforementioned resonance occurs only when an incident light beam is a p-polarized light beam. Therefore, in order to make the resonance occur, there is a need to make settings in advance so that a light beam can strike the aforementioned interface as a p-polarized light beam.

If the wave number of the surface plasmon is found from the specific incidence angle $\theta_{sp}$ at which attenuated total reflection (ATR) takes place, the dielectric constant of a liquid sample to be analyzed can be calculated by the following Equation:

$$K_{sp}(\omega) = (\omega/c)\{\in_m(\omega)\in_s\}^{1/2}/\{\in_m(\omega)+\in_s\}^{1/2}$$

where $K_{sp}$ represents the wave number of the surface plasmon, $\omega$ represents the angular frequency of the surface plasmon, c represents the speed of light in vacuum, and $\in_m$ and $\in_s$ represent the dielectric constants of the thin film layer and the liquid sample, respectively.

If the dielectric constant $\in_s$ of a liquid sample is found, the concentration of a specific substance in the liquid sample is found based on a predetermined calibration curve, etc. As a result, the dielectric constant of the liquid sample, that is, the properties of the liquid sample related to the refractive index thereof can be quantitatively analyzed by finding the specific incidence angle $\theta_{sp}$ at which the intensity of the reflected light at the interface drops sharply.

In addition, a leaky mode sensor is known as a similar sensor making use of ATR (for example, see "Spectral Researches," Vol. 47, No. 1 (1998), pp. 21 to 23 and pp. 26 to 27). This leaky mode sensor is constructed basically of a measuring chip, a light source for emitting a light beam, an optical system, and photo detection means. The measuring chip is equipped with a dielectric block; a thin film layer consisting of a cladding layer formed on the top surface of the dielectric block and an optical waveguide layer formed on the cladding layer; and a liquid-sample holding portion for holding a liquid sample on the thin film layer. The dielectric block is formed, for example, into the shape of a prism. The optical system is used to make the light beam enter the dielectric block at various angles of incidence so that a condition for total internal reflection (TIR) is satisfied at the interface between the dielectric block and the cladding layer. The photodetection means measures the intensity of the light beam totally reflected at the interface, and detects the excited state of a waveguide mode, that is, the state of ATR.

In the leaky mode sensor mentioned above, if a light beam strikes the cladding layer through the dielectric block at incidence angles greater than a critical incidence angle at which total internal reflection (TIR) takes place, the light beam is transmitted through the cladding layer. Thereafter, in the optical waveguide layer formed on the cladding layer, only light with a specific wave number, incident at a specific incidence angle, propagates in a waveguide mode. If the waveguide mode is excited in this manner, most of the incident light is confined within the optical waveguide layer, and consequently, ATR occurs in which the intensity of light totally reflected at the aforementioned interface drops sharply. Since the wave number of the light propagating through the optical waveguide layer depends upon the refractive index of the liquid sample on the optical waveguide layer, the refractive index of the liquid sample and the properties of the liquid sample related to the refractive index can be analyzed by finding the aforementioned specific incidence angle $\theta_{sp}$ at which ATR takes place.

There are cases where in the field of pharmaceutical research, the above-mentioned surface plasmon resonance sensor and leaky mode measuring sensor are employed in the research of the interaction between a desired sensing substance and a liquid sample. For instance, the sensors are employed in the measurement of interaction, such as the bonding reaction between a specific substance contained in a liquid sample and a sensing substance and the dissociating reaction of a specific substance into a liquid sample from a bonded substance. Such interaction includes protein-protein interaction, DNA-protein interaction, sugar-protein interaction, protein-peptide interaction, lipid-protein interaction, a bond between chemical substances, and so on.

In addition, there are cases where the above-mentioned surface plasmon resonance sensor and leaky mode measuring sensor are used in a random screening method for detecting a specific substance that bonds to a sensing substance. In this case, a sensing substance is fixed on the aforementioned thin film layer. Then, a liquid sample containing various target substances is dropped into the sensing substance, and each time a predetermined time elapses, the state of ATR is measured.

If a target substance in the liquid sample bonds to the sensing substance, the refractive index of the sensing substance changes with the lapse of time by the bond therebetween. Therefore, the state of ATR is measured at predetermined intervals and it is measured whether a change has occurred in the state of ATR. In this manner, it can be decided whether there is a bond between a target substance and a sensing substance, that is, whether the target substance is a specific substance that bonds to the sensing substance. As a combination of a specific substance and a sensing substance, there are a combination of an antigen and an antibody and a combination of an antibody and an antibody. For example, a rabbit antihuman immunoglobulin G (IgG) antibody is fixed to a measuring chip as a sensing substance, and a human IgG antibody is employed as a specific substance.

Note that the present applicant has proposed a sensor, utilizing ATR, for making measurements by employing a measuring chip which has a plurality of liquid-sample holding portions (see Japanese Patent Application No. 2001-397411). The use of such a sensor makes it possible to measure a plurality of samples in a short time.

However, in the conventional sensors utilizing ATR which have been proposed, the state of ATR described above is measured after a liquid sample is supplied to a cup-shaped or dish-shaped liquid-sample holding portion having a thin film layer previously formed on the inner bottom surface thereof.

Because of this, when a measurement is made after the supply of a liquid sample, there is a possibility that (1) the liquid sample will evaporate, (2) the concentration of the liquid sample will change, and (3) the accuracy of the measurement of ATR will be reduced.

Particularly, in the case of measuring a temporal change in the interaction between the sensing substance and liquid sample in a measuring chip, measurements are often made for extensive periods of time and therefore there is a possibility that during the measurements, the liquid sample will evaporate and an accurate measurement of the temporal change cannot be made.

SUMMARY OF THE INVENTION

The present invention has been made in view of the circumstances mentioned above. Accordingly, it is the primary object of the present invention to provide a sensor and a measuring chip assembly, utilizing ATR, which are capable of preventing evaporation of a liquid sample and enhancing the measurement accuracy of the state of ATR.

To achieve this end and in accordance with the present invention, there is provided a sensor utilizing attenuated total reflection, comprising:

a light source for emitting a light beam;
a measuring chip comprising
a dielectric block transparent to the light beam, a thin film layer formed on the top surface of the dielectric block, and one or a plurality of liquid-sample holding portions for holding a liquid sample on the thin film layer;
an optical system for making the light beam enter the dielectric block at various angles of incidence so that a total internal reflection condition is satisfied at an interface between the dielectric block and the thin film layer;
photodetection means for detecting intensity of the light beam totally reflected at the interface; and
measurement means for measuring a state of attenuated total reflection, based on the result of detection obtained by the photodetection means;
wherein the liquid-sample holding portion of the measuring chip has an opening at its top surface;
and wherein the sensor further comprises lid-means supply means for placing lid means on the opening to prevent evaporation of the liquid sample.

As such a sensor, there is a surface plasmon resonance sensor employing a metal film as the aforementioned thin film layer, or a leaky mode sensor in which a cladding layer, formed on one surface of a dielectric block, and an optical waveguide layer, formed on said cladding layer, are employed as the aforementioned thin film layer.

In addition, in the sensor according to the present invention, there are various methods for measuring the intensity of the light beam totally reflected at the aforementioned interface by photodetection means and then analyzing a substance contained in a liquid sample.

For example, a light beam is caused to strike the aforementioned interface at various angles of incidence so that a total internal reflection condition is satisfied at the interface. Then, the intensity of the light beam totally reflected at the interface is measured at each position corresponding to each incidence angle. Based on the intensity, the position (angle) of a dark line generated due to ATR is detected. In this way, a substance in a liquid sample can be analyzed.

In addition, a substance in a liquid sample can be analyzed by making a light beam with a plurality of wavelengths enter a measuring unit at angles of incidence so that a total internal reflection condition is satisfied at the interface, then measuring the intensity of the light beam totally reflected at the interface for each wavelength, and measuring the degree of ATR for each wavelength (see D. V. Noort, K. Johansen, C. -F. Mandenius, Porous Gold in Surface Plasmon Resonance Measurement, EUROSENSORS XIII, 1999, pp. 585–588).

Furthermore, a sample can be analyzed by making a light beam enter a measuring unit at an angles of incidence so that a total internal reflection condition is satisfied at the aforementioned interface, then splitting the light beam into two light beams before the light beam strikes the interface, then causing one of the two light beams to interfere with the other light beam totally reflected at the interface, and measuring the intensity of the light beam after the interference (see P. I. Nikitin, A. N. Grigorenko, A. A. Beloglazov, M. V. Valeiko, A. I. Savchuk, O. A. Savchuk, Surface Plasmon Resonance Interferometry for Micro-Array Biosensing, EUROSENSORS XIII, 1999, pp. 235–238).

In the sensor of the present invention, a sensing substance that bonds to the aforementioned liquid sample may be placed on the thin film layer, and the aforementioned measurement means may measure a temporal change in the state of attenuated total reflection, based on a plurality of detection results obtained at predetermined intervals by the aforementioned photodetection means.

In the case where oil is employed as the aforementioned lid means, the aforementioned lid-means supply means supplies the oil to the aforementioned opening. In the case where the lid means is a lid, the lid-means supply means places the lid on the opening.

The aforementioned lid may have a hole smaller than the aforementioned opening. The lid may be formed into the shape of a reed screen capable of expansion and contraction. In addition, the lid may be formed into a sheet shape.

Note that it is preferable that in the aforementioned liquid-sample holding portion with the lid means placed on the opening, the amount of liquid that evaporates per hour is 2% or less. It is further desirable that the amount of liquid that evaporates per hour is 0.5% or less.

In accordance with the present invention, there is provided a measuring chip assembly comprising:

a measuring chip, which is employed in the sensor utilizing attenuated total reflection, comprising
a dielectric block transparent to the light beam, a thin film layer formed on the top surface of the dielectric block, and one or a plurality of liquid-sample holding portions for holding a liquid sample on the thin film layer; and
a lid provided on the opening of the measuring chip.

In the measuring chip assembly of the present invention, the aforementioned lid may have a hole smaller than the opening. In addition, the lid may be formed into the shape of a reed screen capable of expansion and contraction, or a sheet shape.

Note that it is preferable that in the aforementioned liquid-sample holding portion with the lid means placed on the opening, the amount of liquid that evaporates per hour is 2% or less. It is further desirable that the amount of liquid that evaporates per hour is 0.5% or less.

Note that the aforementioned liquid-sample holding portion is formed on a dielectric block made, for example, of transparent resin, etc. The liquid-sample holding portion has a liquid-sample holding hole. The liquid-sample holding hole is formed into a truncated cone shape so that the thin film layer is exposed to the outside. Within one measuring chip, one or a plurality of liquid-sample holding portions may be provided. In the case where a plurality of liquid-sample holding portions are provided within one measuring chip, the liquid-sample holding portions may be arranged in a row, or they may be arranged in a plurality of rows. In addition, in the case where a plurality of liquid-sample holding portions are provided within one measuring chip, the light source, the optical system, the photodetection means, and the measurement means may be provided for each of the liquid-sample holding portions. In the case of one light source, one optical system, one photodetection means, and one measurement means, they may be serially moved, or the measuring chip may be moved.

In the case in which a measuring chip with a plurality of liquid-sample holding portions is employed, a plurality of lids may be placed on the openings of the liquid-sample holding portions, respectively. In addition, the plurality of lids may be integrated into a single lid.

In the aforementioned sensor of the present invention, lid means to prevent evaporation of a liquid sample is placed on the opening of the liquid-sample holding portion of a measuring chip. Thus, evaporation of the liquid sample supplied to the liquid-sample holding portion is prevented, whereby accuracy of measurement can be enhanced.

When measuring a temporal change in the interaction between the sensing substance and the liquid sample held in the measuring chip, evaporation of the liquid sample is prevented even if measurements are made for an extensive period of time. Thus, an accurate temporal change can be measured.

In the case where the oil supplied to the aforementioned opening is employed as the lid means, it can be easily placed on the opening.

In the case where a lid fitted in the opening is employed as the lid means, evaporation of the liquid sample can be prevented, while the entrance of dust into the liquid sample supplied to the liquid-sample holding portion can also be prevented.

In the case where the aforementioned lid has a hole, a liquid sample can be supplied through the hole. Therefore, the lid can be placed on the opening of the liquid-sample supply mechanism before the liquid sample is supplied to the liquid-sample holding portion.

If a lid is formed in the shape of a reed screen capable of expansion and contraction, a liquid sample can be supplied through the reed screen. Therefore, the lid can be placed on the opening of the liquid-sample supply mechanism before the liquid sample is supplied to the liquid-sample holding portion. In addition, there is no need to perform precise alignment when a liquid sample is supplied.

If a lid is formed into a sheet shape, there is no need to perform precise alignment when the lid is placed on the aforementioned opening, and the lid can be easily placed on the opening.

In the liquid-sample holding portion with lid means (or a lid) placed on the opening, if the amount of liquid that evaporates per hour is 2% or less, a change in the refractive index of a liquid sample resulting from evaporation of the liquid sample hardly occurs and therefore measurements can be made with a high degree of accuracy.

Further, if the amount of liquid that evaporates per hour is 0.5% or less, even less of the liquid sample evaporates, and measurements can be made with an even higher degree of accuracy.

Furthermore, in the case where a measuring chip with a plurality of liquid-sample holding portions is employed, a plurality of lids can be integrated and employed. In this case, lids can be placed on the openings of the liquid-sample holding portions by a single operation and therefore the lids can be efficiently placed.

BRIEF DESCRIPTION OF THE DRAWINGS

The present invention will be described in further detail with reference to the accompanying drawings wherein:

FIG. 9 is a perspective view showing a surface plasmon resonance sensor constructed according to a third embodiment of the present invention;

DESCRIPTION OF THE PREFERRED EMBODIMENTS

Embodiments of the present invention will hereinafter be described in detail with reference to the drawings.

Figure 1:
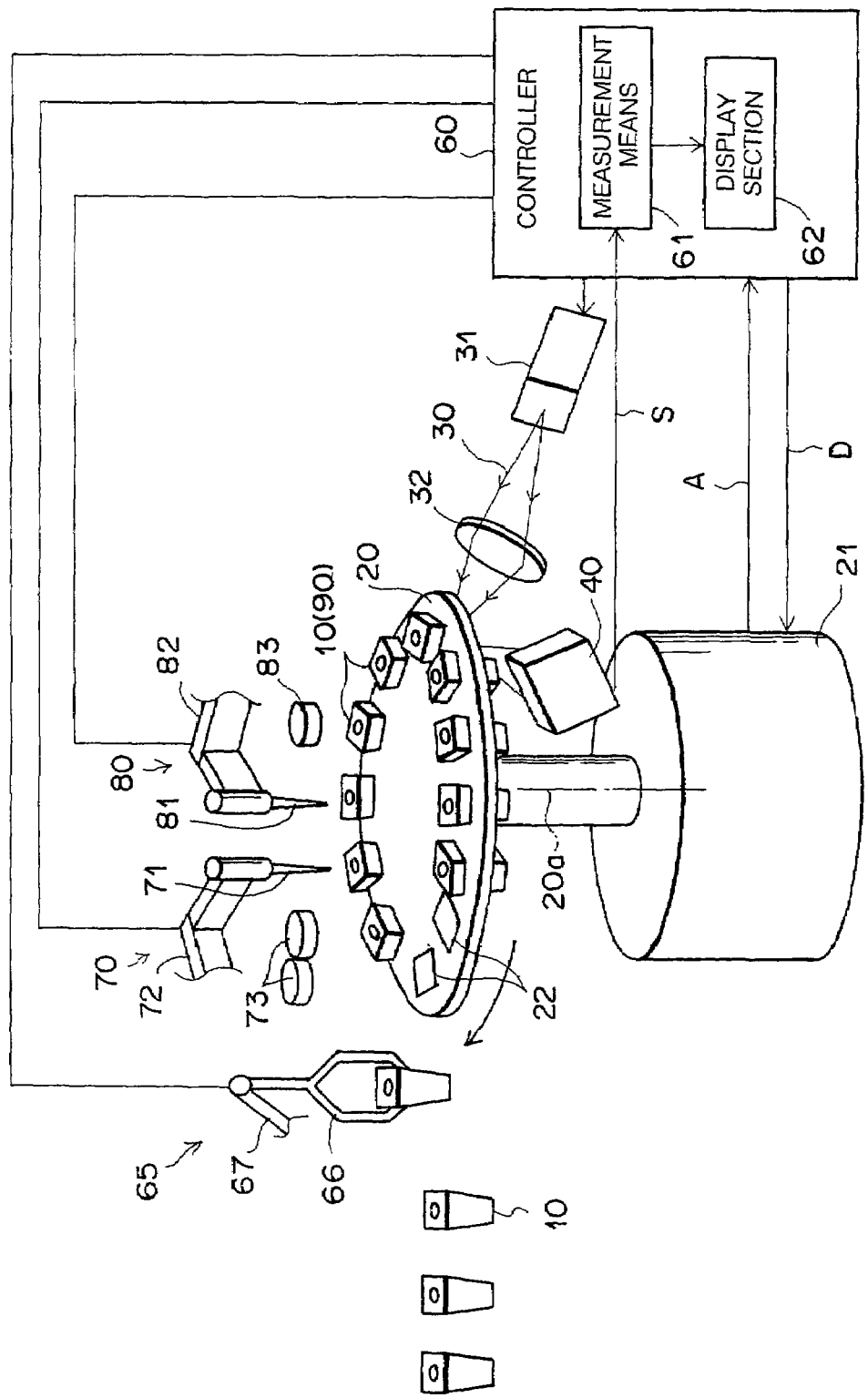
FIG. 1 is a perspective view showing a surface plasmon resonance sensor constructed according to a first embodiment of the present invention.
Figure 2:
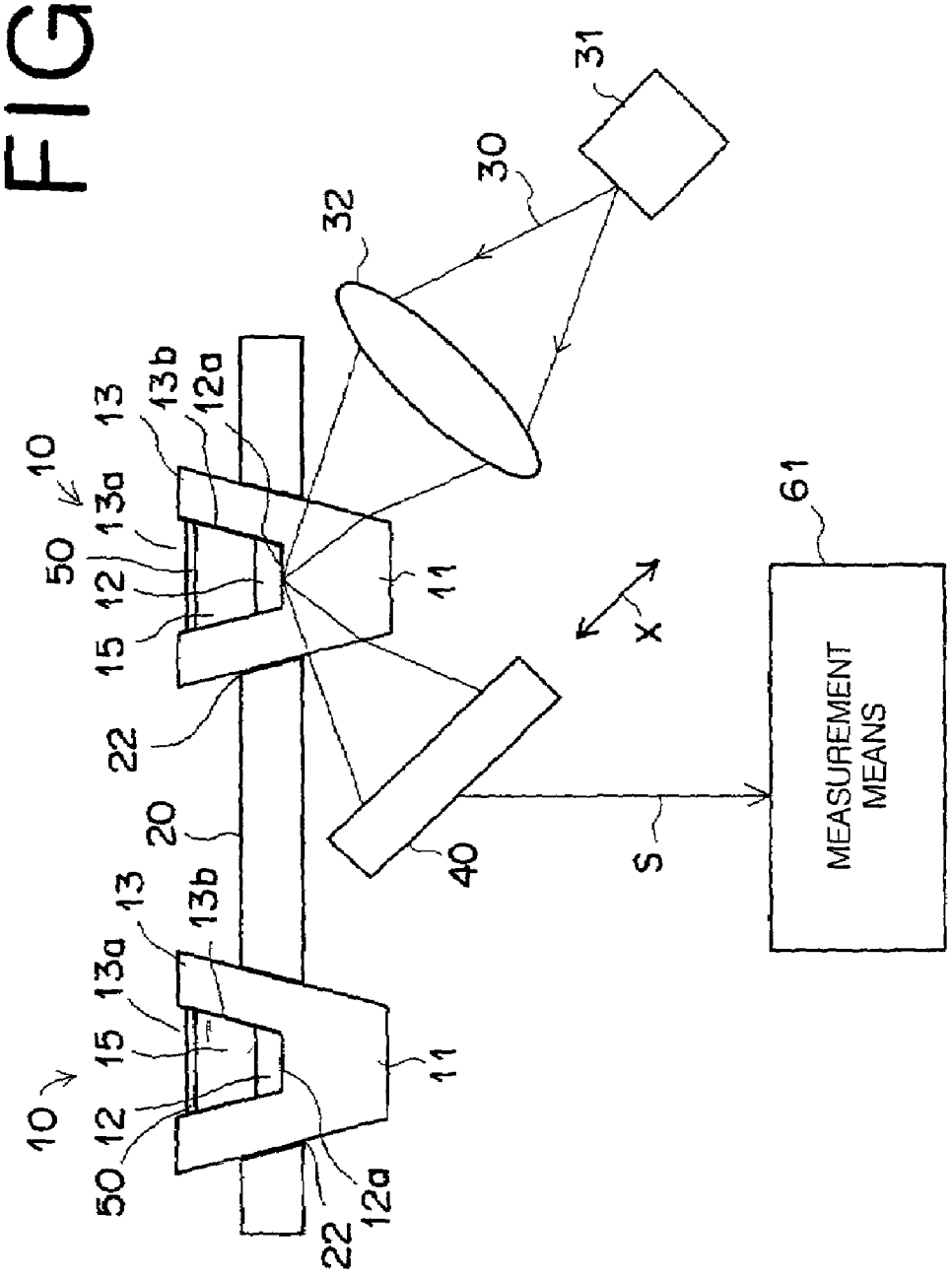
FIG. 2 is a part-sectional side view showing the essential parts of the surface plasmon resonance sensor shown in FIG. 1.

FIG. 1 shows a surface plasmon resonance sensor constructed according to a first embodiment of the present invention, and FIG. 2 shows a side view of the essential parts thereof. As shown in the figures, the surface plasmon resonance sensor has a plurality of measuring units 10; a turntable 20 for supporting the measuring units 10; and supporting-body drive means (movement means) 21 for rotating the turntable 20 intermittently. The surface plasmon resonance sensor also has a laser light source 31, such as a semiconductor laser, etc., for emitting a measuring light beam (e.g., a laser beam) 30; condenser lens 32 constituting an optical incidence system; and a photodetector 40. The surface plasmon resonance sensor further has a controller 60 for controlling the laser light source 31 and the supporting-body drive means 21; a measuring-unit supply mechanism 65 for supplying or removing the measuring unit 10 to or from the turntable 20; and a liquid-sample supply mechanism 70. The controller 60 receives an output signal S from the photodetector 40 and carries out a process that is to be described later. Furthermore, the surface plasmon resonance sensor has an oil supply mechanism 80 as lid-means supply means. Note that the measuring unit 10 functions as a measuring chip of the present invention.

The measuring unit 10, as shown in FIG. 2, is constructed of a dielectric block 11 and a metal film 12. The dielectric block 11 is formed, for example, into a generally truncated quadrangular pyramid shape. The metal film 12 is formed on the top surface of the dielectric block 11 and is made, for example, of silver, copper, aluminum, etc.

The dielectric block 11 is made, for example, of transparent resin, etc. A liquid sample holder 13 is formed on the dielectric block 11 and has a liquid-sample holding portion 13b. The liquid-sample holding portion 13b is formed into a truncated cone shape, and has an opening 13a so that the metal film 12 is exposed to the outside. The liquid sample holder 13 stores a liquid sample 15 in the liquid-sample holding portion 13b.

The turntable 20 has a plurality of through holes 22 in which the measuring units 10 are fitted. In the first embodiment, 12 (twelve) through holes 22 are provided on a circle at equiangular intervals with respect to the rotation axis 20a of the turntable 20. The measuring units 10 are exchangeable with respect to the turntable 20. The supporting-body drive means 21 is constructed of a stepping motor, etc., and is rotated intermittently at intervals of an angle equal to the pitch between the through holes 22.

The condenser lens 32, as shown in FIG. 2, collects the light beam 30 and makes the light beam 30 enter the dielectric body 11 so that the light beam 30 converges on the interface 12a between the dielectric block 11 and the metal film 12. Thus, the light beam 30 enters the dielectric block 11 so that it includes components incident on the interface 12a at various angles of incidence. The incidence angle range includes an angle range in which a total internal reflection condition for the light beam 30 is satisfied at the interface 12a, and in which surface plasmon resonance can occur.

Note that the light beam 30 strikes the interface 12a as a p-polarized light beam. For this reason, it is necessary to dispose the laser light source 31 so that the polarization direction thereof becomes a predetermined direction. Alternatively, the polarization direction of the light beam 30 may be controlled with a wavelength plate, a polarizing plate, etc.

The photodetector 40 is a line sensor consisting of a large number of light-receiving elements. The light-receiving elements are arranged in a row in the direction of arrow X in FIG. 2.

On the other hand, the controller 60 receives an address signal A, representing a position at which rotation of the supporting-body drive means 21 is stopped, from the supporting-body drive means 21. Based on a predetermined sequence, this controller 60 also outputs a drive signal D which causes the supporting-body drive means 21 to operate. The controller 60 is equipped with measurement means 61 to which the output signal S from the aforementioned photodetector 40 is input, and a display section 62 to which an output signal from the signal processing section 61 is input. The controller 60 is connected with the measuring-unit supply means 65, the liquid-sample supply mechanism 70, and the oil supply mechanism 80, and controls operation of them as needed.

The measuring-unit supply mechanism 65 is constructed of a holding portion 66 for holding the measuring unit 10, and means 67 for moving the holding portion 66.

The liquid-sample supply mechanism 70 is constructed of a pipette 71 for holding a predetermined amount of liquid sample by suction, and means 72 for moving the pipette 71. The liquid-sample supply mechanism 70 suctions and holds a liquid sample from a liquid-sample container 73 situated at a predetermined position through the pipette 71, and drops the liquid sample into the liquid-sample holding portion 13b of the measuring chip 10 being at a predetermined stop position.

The oil supply mechanism 80 is constructed of a pipette 81 for holding a predetermined amount of oil 50 by suction, and means 82 for moving the pipette 81. The oil supply mechanism 80 suctions and holds oil from an oil container 83 situated at a predetermined position through the pipette 81, and drops the oil 50 into the liquid-sample holding portion 13b of the measuring chip 10 through the opening 13a. Note that mineral oil (manufactured by Applied Biosystems) is employed as the oil 50.

A description will hereinafter be given of how a sample is analyzed by the surface plasmon resonance sensor constructed as described above. Measuring units 10 are prepared and arranged, for example, in a 96-hole cassette (not shown). The measuring units 10 are fitted serially in the through holes 22 in the turntable 20 by the measuring-unit supply mechanism 65. The turntable 21 is rotated intermittently by the supporting-body drive means 50, as mentioned previously. When the turntable 20 is stopped, the liquid sample 15 is supplied by the liquid-sample supply mechanism 70 to the sample holding portion 13b of the measuring chip 10 being at a predetermined position.

When the turntable is further rotated and the measuring unit 10 with the liquid sample 15 supplied thereto is moved to the position where the oil supply mechanism 80 is provided, then the oil 50 is supplied to the liquid-sample holding portion 13b of the measuring unit 10 through the opening 13a by the oil supply mechanism 80. The amount of oil that is supplied to the liquid-sample holding portion 13b is determined according to the surface area of the liquid sample 15 within the liquid-sample holding portion 13b. Generally, if oil of 20 microliters or greater per surface area 20 mm$^2$ of the liquid sample 15 is supplied, then the whole surface of the liquid sample 15 is covered with the oil 50. Because of this, in the liquid-sample holding portion 13b underneath the oil 50, the amount of liquid that evaporates per hour becomes 2% or less and therefore the sample 15 hardly evaporates during measurement.

Thereafter, when the turntable 20 is rotated a few times and stopped, the measuring chip 10 holding the liquid sample 15 in the sample holding portion 13b is moved to a measuring position (for example, the position of the measuring chip 10 on the right side in FIG. 2) where the above-mentioned light beam 30 enters the dielectric block 11. If the measuring chip 10 is held at the measuring position, the laser light source 31 is driven in response to a signal from the controller 60. Then, the light beam 30 emitted from the laser light source 31 is collected and directed to the dielectric block 11 and converges on the interface 12a between the dielectric block 11 and the metal film 12. The light beam 30 totally reflected at the interface 12a is detected by the photodetector 40.

The light beam 30 includes components incident on the interface 12a at various incidence angles θ, because it enters the dielectric block 11 and converges on the interface 12a, as described above. Note that these incidence angles θ are greater than a critical incidence angle at which total internal reflection (TIR) occurs. Therefore, the light beam 30 is totally reflected at the interface 12a, and the reflected light beam 30 includes components reflected at various angles of reflection.

Figure 3:
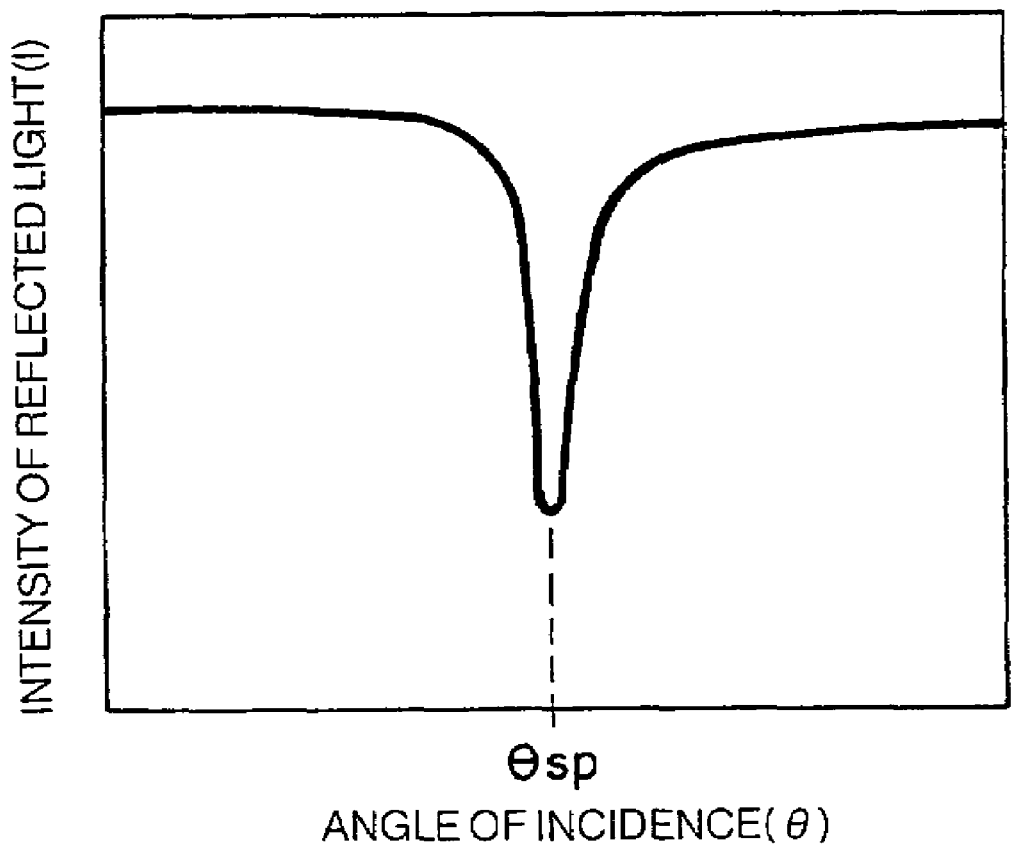
FIG. 3 is a graph showing the relationship between the incidence angle at which a light beam enters the measuring unit of the surface plasmon resonance sensor, and the intensity of the light beam reflected at the measuring unit.

When the light beam 30 is totally reflected at the interface 12a, as described above, an evanescent wave propagates on the side of the metal film 12 through the interface 12a. In the case in which the light beam 30 strikes the interface 12a at a specific incidence angle $\theta_{sp}$, the evanescent wave resonates with the surface plasmon excited on the surface of the metal film 12. Because of this, the intensity I of the light reflected at the interface 12a drops sharply. The relationship between the incidence angle θ of the light beam 30 with respect to the interface 12a and the intensity I of the light beam 30 reflected at the interface 12a is shown in FIG. 3.

Hence, to detect the state of attenuated total reflection (ATR), the measurement means 61 measures the quantity of light detected by each light-receiving element, from the signal S output from the photodetector 40. And based on the position of the light-receiving element that detected a dark line (corresponding to ATR), the measurement means 61 detects the specific incidence angle $\theta_{sp}$ (at which ATR occurs). In addition, a specific substance in the liquid sample 15 can be quantitatively analyzed from the aforementioned relationship between the intensity I and the incidence angle θ, shown in FIG. 3. Based on the principle described above, a specific substance in the liquid sample 15 is quantitatively analyzed and the result of analysis is displayed on the display section 62. The measuring unit 10 for which measurements have been completed is removed from the turntable 20 by the measuring-unit supply mechanism 65.

In the first embodiment, the liquid sample 15 is first supplied to the liquid-sample holding portion 13b and then the oil 50 is supplied to the liquid-sample holding portion 13b. Because of this, the surface of the liquid sample 15 is covered with the oil 50, and under the oil 50, the amount of liquid that evaporates per hour becomes 2% or less. Because of this, the liquid sample 15 hardly evaporates during measurement, the concentration of the liquid sample 15 is kept constant, and the generation of evaporation heat can be prevented. Thus, the measurement accuracy of the state of ATR is enhanced. In addition, since oil is employed as lid means, the opening 13a of the liquid-sample holding portion 13b can be easily covered with the lid means. Note that it is further desirable to make the amount of liquid that evaporates per hour to be 0.5% or less.

In the first embodiment described above, while the turntable 20 is employed to support the measuring units 10, the present invention is not limited to the structure of the turntable 20. For example, the turntable 20 may be rotated in the reverse direction as well so that the measuring units 10 can be measured again by the optical measurement mechanism, constructed of the light source 31, the condenser lens 32, and the photodetector 40. In addition, a plurality of optical measurement mechanisms can be provided so that one measuring unit 10 can be measured a plurality of times during the time the turntable 20 makes one revolution. Furthermore, the supporting body for a plurality of measuring units 10 may be moved reciprocally or in X and Y directions, and the plurality of measuring units 10 may be serially set in one or a plurality of optical measurement mechanisms by moving the supporting body.

As a first modification of the first embodiment, the optical measurement mechanism can be moved with respect to the supporting body to serially measure the measuring units 10, or both the supporting body and the optical measurement mechanism can be moved to serially measure the measuring units 10. As with the first embodiment, a plurality of measuring units 10 can be measured in a short time.

As a second modification of the first embodiment, a sensing substance can be fixed on the metal film 12, and it can be decided whether or not a target substance in a liquid sample is a specific substance that bonds to this sensing substance. In the second modification, a temporal change in the aforementioned specific incidence angle $\theta_{sp}$ (at which ATR occurs) is measured, and in the case where the specific incidence angle $\theta_{sp}$ changes greatly, it is judged that a target substance in a liquid sample is the specific substance. To perform such a judgment, there is a need to measure one measuring unit 10 a plurality of times. In this case, if the measuring unit 10 remains supported by the turntable 20 after a first measurement, the measuring unit 10 can be measured again by rotation of the turntable 20. When one measuring unit 10 is thus measured for an extensive period of time, there is a possibility that the concentration of the liquid sample 15 will change due to evaporation of the liquid sample 15. However, since the surface of the liquid sample 15 is covered with oil, evaporation of the liquid sample 15 is prevented and the accuracy of the measurement of a temporal change in the state of ATR is enhanced.

Figure 4:
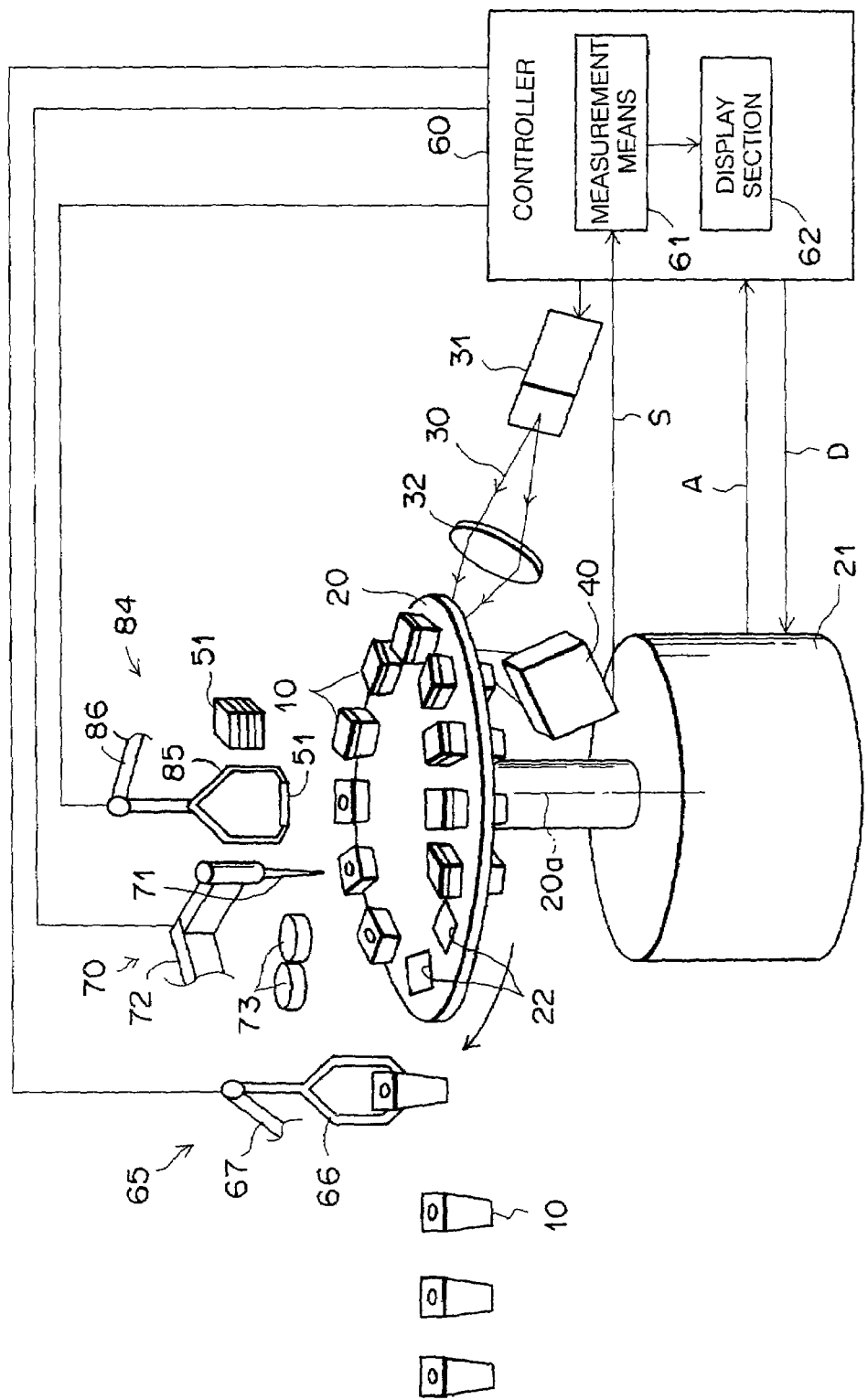
FIG. 4 is a perspective view showing a surface plasmon resonance sensor constructed according to a second embodiment of the present invention.
Figure 5A:
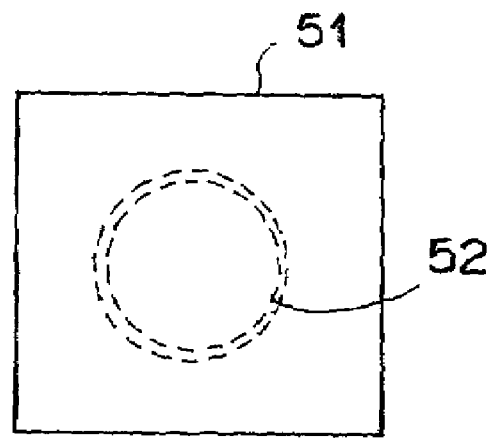
FIG. 5A is a top view showing the lid of FIG. 4.
Figure 5B:
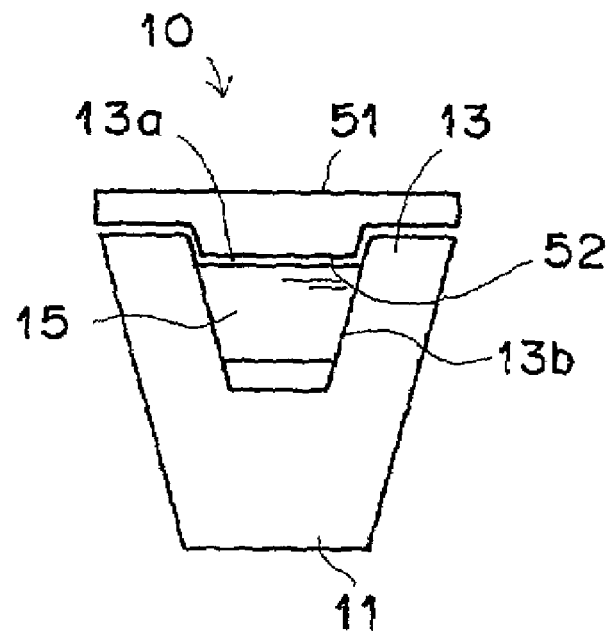
FIG. 5B is a side view showing the lid of FIG. 4.

FIGS. 4 and 5 show a surface plasmon resonance sensor constructed according to a second embodiment of the present invention. Note in FIG. 4 that the same reference numerals are applied to the same parts as those in FIG. 1, and that a description of the same parts will not be given unless particularly necessary.

In the surface plasmon resonance sensor of the second embodiment, a lid supply mechanism 84 to cover the opening 13a of the liquid-sample holding portion 13b of a measuring unit 10 with a lid 51 is employed as lid-means supply means. The lid 51, as shown in FIG. 5, is a square lid with a protruding portion 52 in the form of a truncated cone at the center. The protruding portion 52 is slightly smaller in diameter than the opening 13a of the liquid-sample holding portion 13b. One side of the square of the lid 51 is equal to the length of one side of the top surface of the liquid-sample holder 13. The lid supply mechanism 84 is constructed of a holding portion 85 for holding the lid 51 and means 86 for moving the holding portion 85, and is controlled by a controller 60.

When analyzing samples by the surface plasmon resonance sensor of the second embodiment, the measuring units 10 arranged in a 96-hole cassette (not shown) are fitted serially in the through holes 22 of a turntable 20 by a measuring-unit supply mechanism 65, as with the first embodiment. A liquid sample 15 is supplied by a liquid-sample supply mechanism 70 to the measuring unit 10 held in the through hole 22.

When the turntable 20 is rotated after the supply of the liquid sample 15, and the measuring unit 10 with the liquid sample 15 supplied thereto is moved to the position where the oil supply mechanism 80 is provided, then a lid 50 is placed on the measuring unit 10 by the lid supply mechanism 84. That is, the lid supply mechanism 84 holds one lid 51 with the holding portion 85 from a plurality of lids 51 stacked with the protruding portions 52 downward, and places the lid 51 on the measuring unit 10 so that the protruding portion 52 is fitted in the opening 13a of the liquid-sample holding portion 13b.

By fitting the lid 51 in the opening 13a of the liquid-sample holding portion 13b with the lid supply mechanism 84, evaporation of the liquid sample 15 is prevented and accuracy of measurement is enhanced. In addition, the entrance of dust into the liquid sample 15 supplied to the liquid-sample holding portion 13b can be prevented.

Figure 6A:
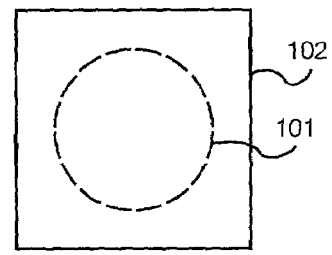
FIG. 6A is a top view showing a first modification of the lid of FIG. 4.
Figure 6B:
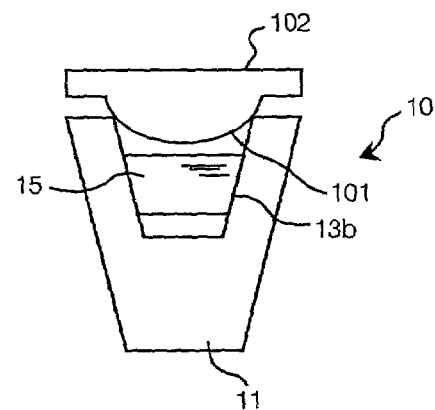
FIG. 6B is a side view showing the first modification.
Figure 7A:
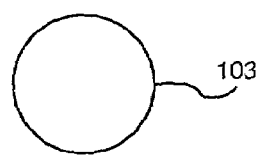
FIG. 7A is a top view showing a second modification of the lid of FIG. 4.
Figure 7B:
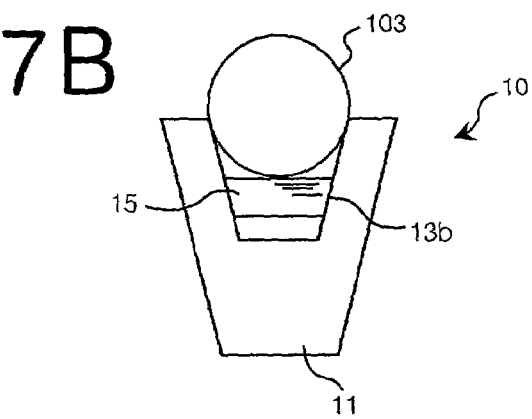
FIG. 7B is a side view showing the second modification.
Figure 8:
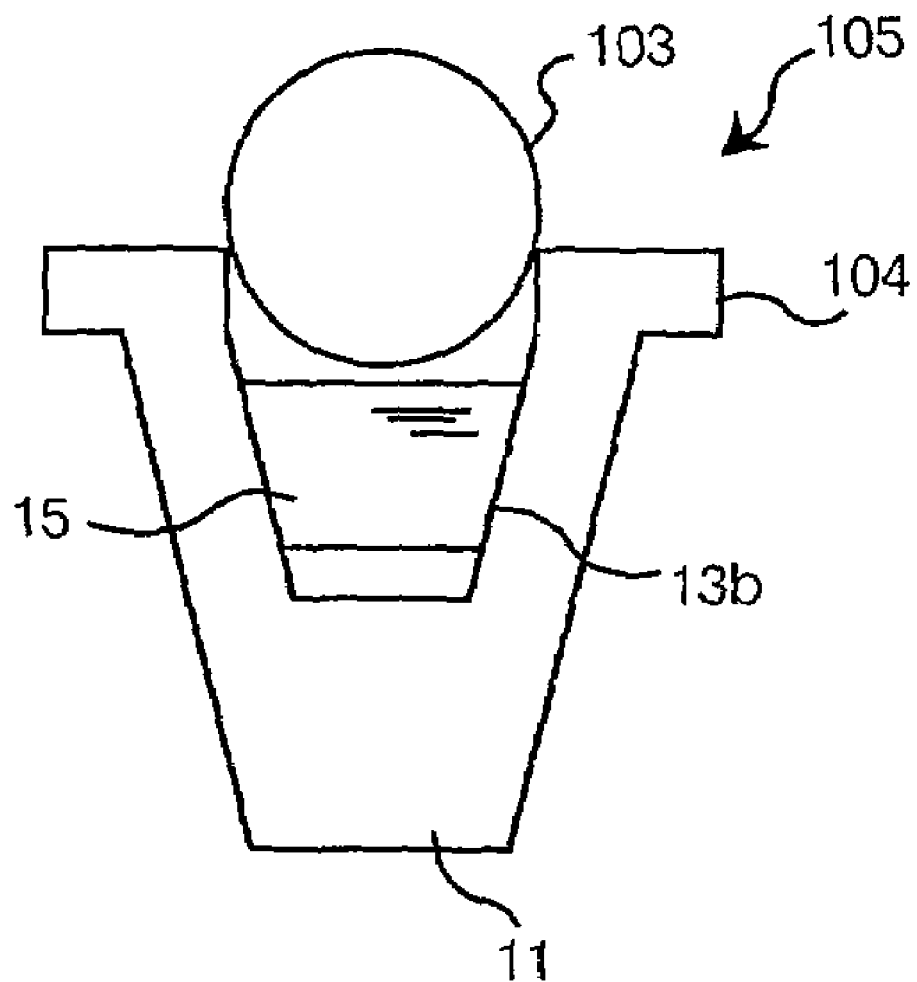
FIG. 8 is a side view showing a modification of the measuring unit of FIG. 4.

As a modification of the lid 51, there is a square lid 102 such as that shown in FIGS. 6A and 6B. The lid 102 has a bowl-shaped protruding portion 101 at the center, and the protruding portion 101 is slightly greater in diameter than the opening 13a of the liquid-sample holding portion 13b. If such a lid 102 is employed, there is no need to perform precise alignment when placing the lid 102 on the measuring unit 10. As another modification of the lid 53, there is a spherical lid 103 such as the one shown in FIGS. 7A and 7B. When placing the lid 103 on the measuring unit 10, the alignment therebetween becomes easier. If a measuring unit 105 with a flange portion 104, such as that shown in FIG. 8, is employed when employing such a lid 103, ample space to hold the liquid sample 15 can be ensured within the measuring unit 105.

Note that if soft resin or rubber is employed as the material of the above-mentioned lid, the close contact property between the opening 13a and the lid is enhanced and therefore evaporation of the liquid sample 15 can be further prevented. In addition, if a sealant, such as oil, etc., is employed between the upper portion of the measuring unit and the lid, the close contact property therebetween is further enhanced.

FIGS. 9 and 10 show a surface plasmon resonance sensor constructed according to a third embodiment of the present invention. Note in FIG. 10 that the same reference numerals are applied to the same parts as those in FIG. 1, and that a description of the same parts will not be given unless particularly necessary.

Figure 10A:
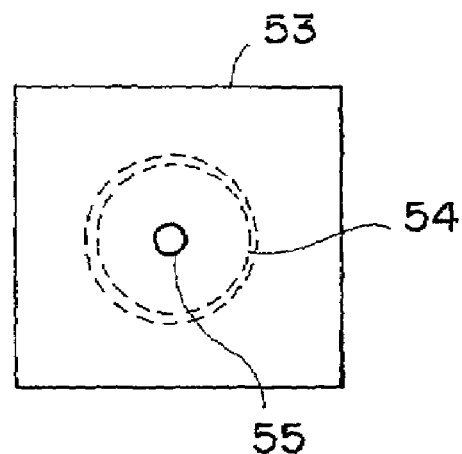
FIG. 10A is a top view showing the lid of FIG. 9.
Figure 10B:
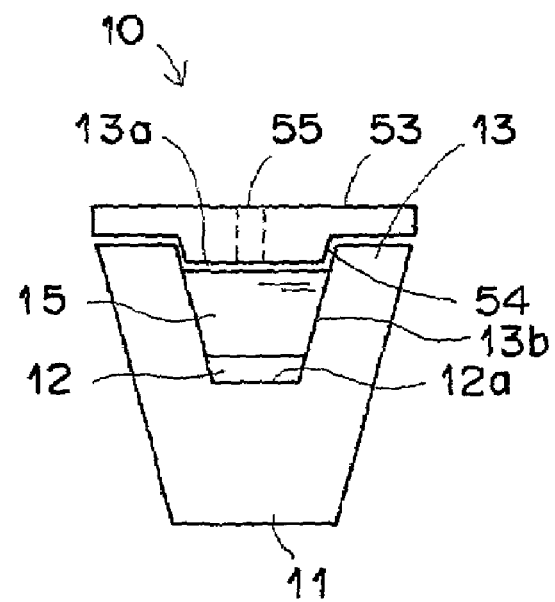
FIG. 10B is a side view showing the lid of FIG. 9.

In the surface plasmon resonance sensor of the third embodiment, a lid supply mechanism 87 to cover the opening 13a of the liquid-sample holding portion 13b of a measuring unit 10 with a lid 53 is employed as lid supply means before the measuring unit 10 is disposed on a turntable 20. The lid 53, as shown in FIGS. 10A and 10B, is a square lid with a protruding portion 54 in the form of a truncated cone at the center. The protruding portion 54 is slightly smaller in diameter than the opening 13a of the liquid-sample holding portion 13b. One side of the square of the lid 53 is equal to the length of one side of the top surface of the liquid-sample holder 13. The protruding portion 54 is provided with a central opening 55 into which the lower end of a pipette 71 of a liquid-sample supply mechanism 70 is inserted.

The lid supply mechanism 87 is constructed of a holding portion 88 for holding the lid 53 and means 89 for moving the holding portion 85, and is controlled by a controller 60.

When samples are analyzed by the surface plasmon resonance sensor of the third embodiment, the lid supply mechanism 87 places lids 53 on the measuring units 10 arranged in a 96-hole cassette (not shown). That is, the lid supply mechanism 87 holds one lid 53 with the holding portion 88 from a plurality of lids 53 stacked with the protruding portions 54 downward, and places the lid 53 on the measuring unit 10 so that the protruding portion 54 of the lid 53 is fitted in the opening 13*a* of the liquid-sample holding portion 13*b*.

The measuring units 10 with the lid 53 placed thereon are fitted serially in the through holes 22 of a turntable 20 by a measuring-unit supply mechanism 65. When the turntable 20 is rotated and the measuring unit 10 is moved to a predetermined position, a liquid sample 15 is supplied to the liquid-sample holding portion 13*b* of the measuring unit 10 by a liquid-sample supply mechanism 70. When the liquid sample 15 is supplied, the pipette 71 of the liquid-sample supply mechanism 70 is inserted into the central opening 55 of the lid 53, and the liquid sample 15 is dropped and supplied.

In the third embodiment, as described above, the lid 53 is placed on the liquid-sample holding portion 13*b* of the measuring unit 10 by the lid supply mechanism 84 before the liquid sample 15 is supplied. Thus, evaporation of the liquid sample 15 is prevented with reliability and accuracy of measurement is further enhanced. In addition, the entrance of dust into the liquid sample 15 supplied to the liquid-sample holding portion 13*b* can be prevented.

Figure 11A:
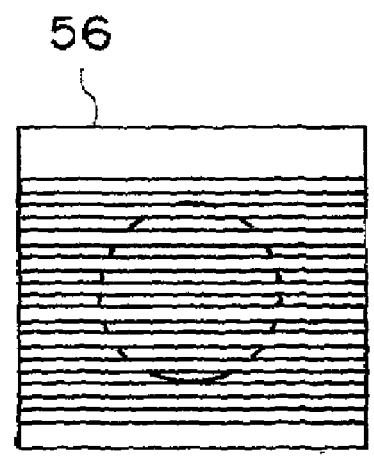
FIG. 11A is a top view showing a first modification of the lid of FIG. 9.
Figure 11B:
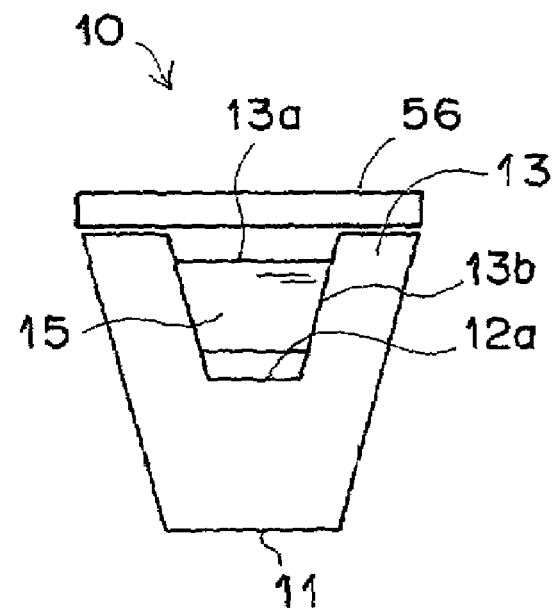
FIG. 11B is a side view showing the first modification.

As a modification of the lid 53 of the third embodiment, there is a square lid 56 such as that shown in FIGS. 11A and 11B. The lid 56 is formed into the shape of a reed screen capable of expansion and contraction. In this case, a pipette 71 can be inserted through the reed screen to supply a liquid sample 15. Thus, there is no need to perform precise alignment when supplying the liquid sample 15.

Figure 12A:
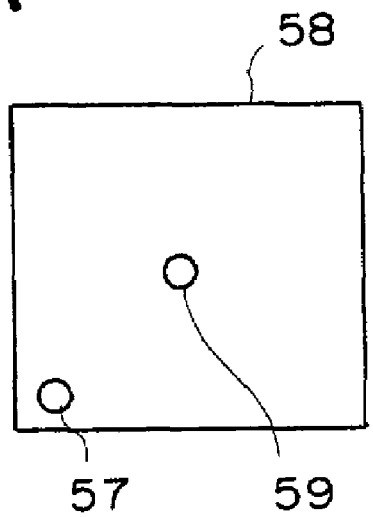
FIG. 12A is a top view showing a second modification of the lid of FIG. 9.
Figure 12B:
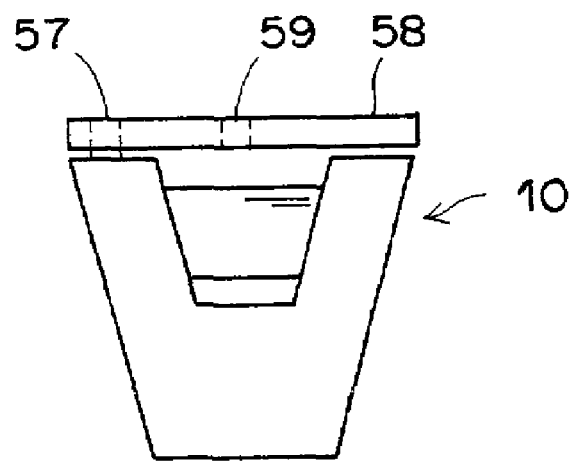
FIG. 12B is a side view showing the second modification.
Figure 13A:
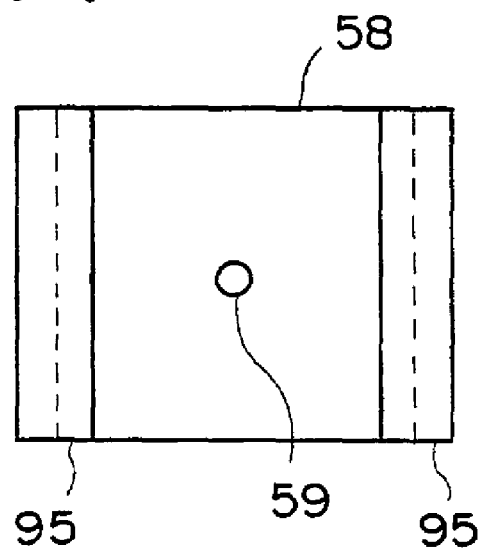
FIG. 13A is a top view showing a third modification of the lid of FIG. 9.
Figure 13B:
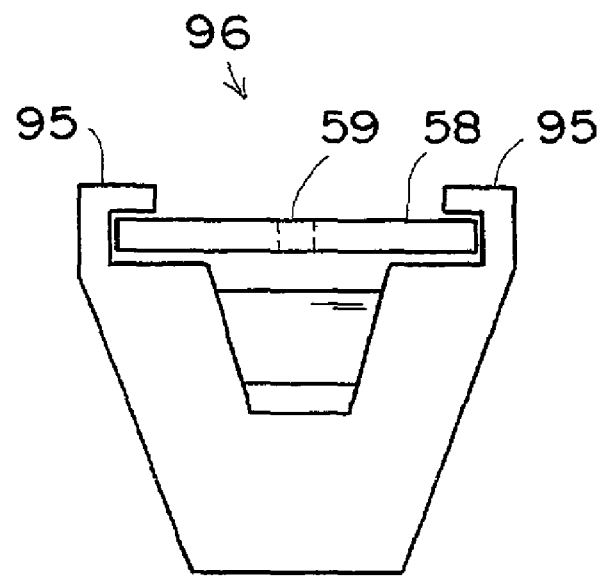
FIG. 13B is a side view showing a modification of the measuring unit of FIG. 9.

As another modification, there is a lid 58 such as that shown in FIGS. 12A and 12B. The lid 58 is mounted on a rotatable shaft 57 erected in the top surface of a measuring unit 10. The lid 58 is formed into the shape of a square plate having a central opening 59. The opening 13*a* of the measuring unit 10 is opened or closed by rotating the lid 58 on the rotatable shaft 57. If the measuring unit 10 is provided with such a lid 58, there is no possibility that the lid 58 will be disconnected from the measuring unit 10, when the measuring unit 10 is moved. As a modification of the measuring unit employing the lid 58, there is a measuring unit 96 such as that shown in FIGS. 13A and 13B. The measuring unit 96 is equipped with a pair of engagement portions 95. If the lid 58 is inserted into the grooves formed in the engagement portions 95, the opening of the measuring unit 96 can be covered with the lid 58. Once the lid 58 is attached to the measuring unit 96, it will not be disconnected from the opening of the measuring unit 96 easily.

Note that in the measuring unit 10 employed in the aforementioned embodiments, the dielectric block 11, the metal film 12, and the liquid-sample holder 13 are formed integrally with one another. However, the present invention can also employ a measuring unit in which the metal film 12 and the liquid-sample holder 13 formed integrally with each other are exchangeable with respect to the dielectric block 11.

Figure 14:
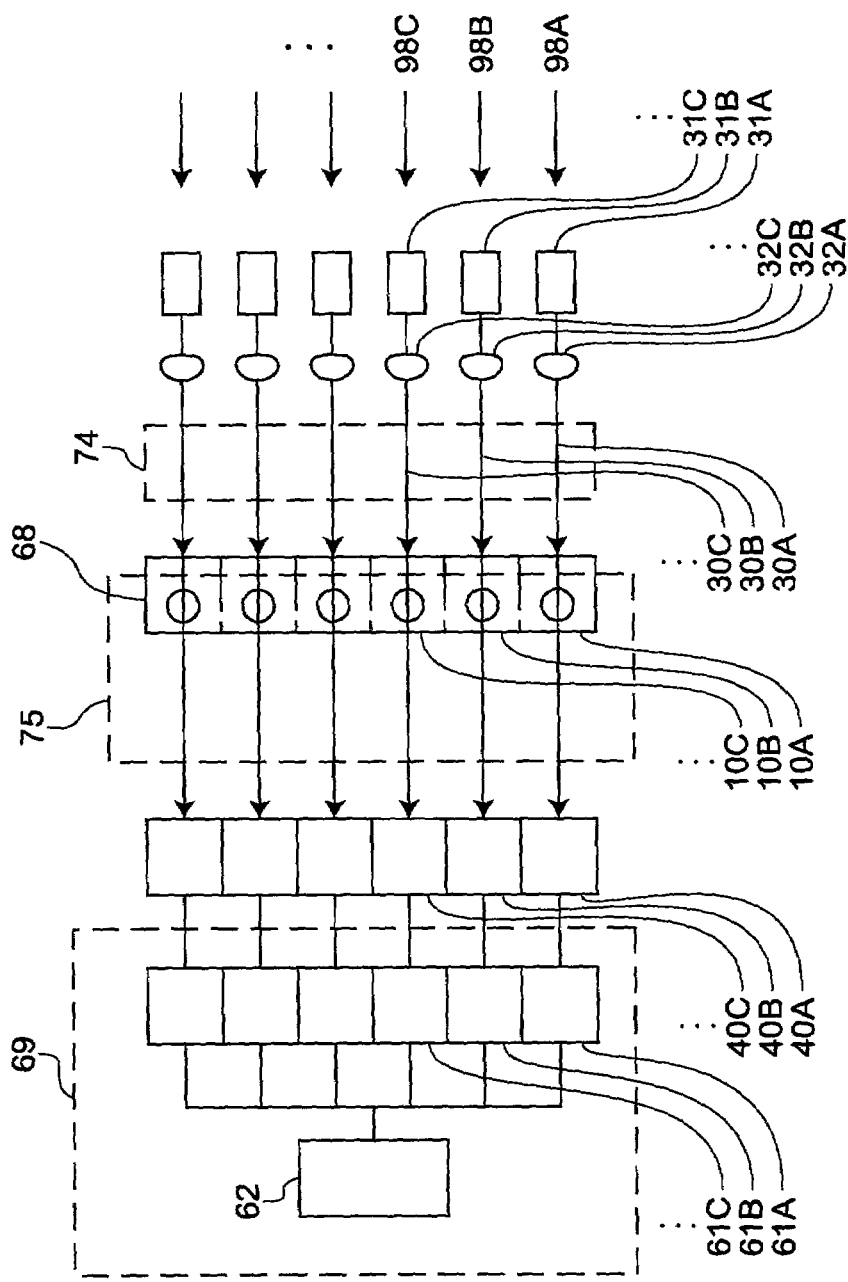
FIG. 14 is a plan view showing a surface plasmon resonance sensor constructed according to a fourth embodiment of the present invention.
Figure 15:
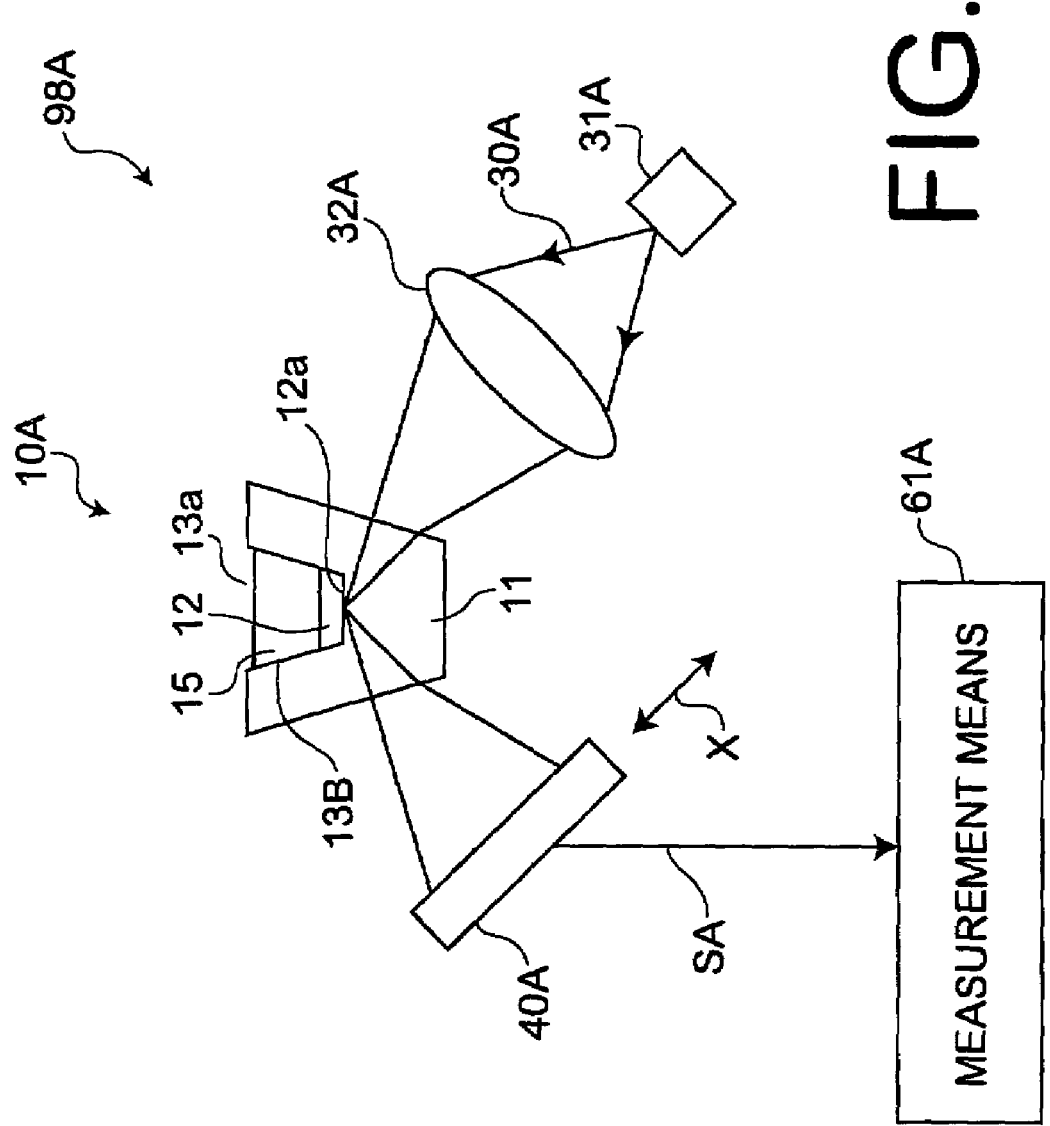
FIG. 15 is a part-sectional side view showing the essential parts of the surface plasmon resonance sensor shown in FIG. 14.
Figure 16:
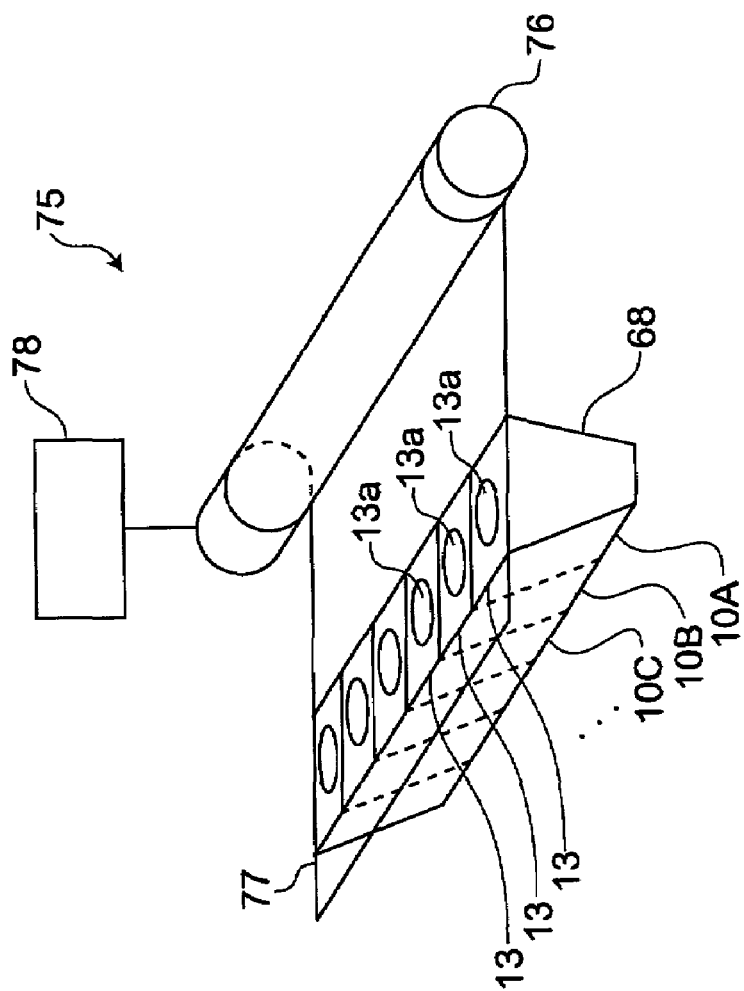
FIG. 16 is a perspective view of the sheet supply mechanism employed in the surface plasmon resonance sensor shown in FIG. 14.

FIGS. 14, 15, and 16 show a surface plasmon resonance sensor constructed according to a fourth embodiment of the present invention. Note in FIGS. 14 and 15 that the same reference numerals are applied to the same parts as those in FIGS. 1 and 2, and that a description of the same parts will not be given unless particularly necessary.

As shown in FIG. 14, in the surface plasmon resonance sensor of the fourth embodiment, the state of ATR is detected by causing light beams 30A, 30B, 30C . . . to enter the measuring units 10*a*, 10B, 10C . . . of a measuring unit array 68.

The surface plasmon resonance sensor is equipped with the measuring unit array 68; laser light sources 31A, 31B, 31C . . . ; condenser lenses 32A, 32B, 32C . . . ; photodetectors 40A, 40B, 40C . . . ; a controller 69; a liquid-sample supply mechanism 74; and a sheet supply mechanism (lid-means supply means) 75. The measuring unit array 68 consists of 6 (six) measuring units 10A, 10B, 10C . . . . The laser light sources 31A, 31B, 31C . . . emit light beams 30A, 30B, 30C . . . , respectively. The condenser lenses 32A, 32B, 32C . . . cause the light beams 30A, 30B, 30C . . . to enter the measuring units 10A, 10B, 10C . . . , respectively. The photodetectors 40A, 40B, 40C . . . receive the light beam reflected at the measuring units 10A, 10B, 10C . . . , respectively. The controller 69 performs signal processing in response to signals SA, SB, SC . . . output from the photodetectors 40A, 40B, 40C . . . . The liquid-sample supply mechanism 74 supplies different kinds of liquid samples to the measuring units 10A, 10B, 10C . . . . Note that the measuring unit array 68 functions as the measuring chip of the present invention.

The measuring units 10A, 10B, 10C . . . have the same structure as the measuring unit 10 shown in FIG. 1, except that the dielectric blocks 11 and the liquid-sample holders 13 of each measuring unit are formed as an integral piece with each other as shown in FIG. 16. By way of example, the measuring unit 10 is schematically shown in FIG. 15.

On the other hand, the controller 69 is equipped with measurement means 61A, 61B, 61C . . . and a display section 62. The measurement means 61A, 61B, 61C . . . receive the signals SA, SB, SC. . . . output from the photodetectors 40A, 40B, 40C . . . . The display section 62 receives the signals output from the measurement means 61A, 61B, 61C . . . . The controller 69 is connected with the liquid-sample supply mechanism 74 and the sheet supply mechanism 75, and controls their operations as needed.

The sheet supply mechanism 75, as shown in FIG. 16, is equipped with a cylindrical sheet holding portion 76; a flexible cover sheet 77 wound on the sheet holding portion 76; and a sheet supply portion 78 for placing the cover sheet 77 onto the openings 13*a* of the liquid-sample holders 13*b* of the measuring unit array 68 as needed by rotating the sheet holding portion 76. The operation of the sheet supply portion 78 is controlled by the controller 69.

The measurement of the state of ATR for one measuring unit (e.g., measuring unit 10A) having a liquid sample 15 supplied thereto is made by a surface plasmon resonance sensor unit 98A, which is constructed of the laser light source 31A, condenser lens 32A, measuring unit 10A, photodetector 40A, and measurement means 61A.

Prior to measurement, the measuring unit array 68 is installed at the measuring position by a measuring-unit array supply mechanism (not shown). At this stage, the cover sheet 77 has been wound on the sheet holding portion 76. The controller 69 causes the liquid-sample supply mechanism 76 to supply different liquid samples 15 to the liquid-sample holding portions 13*b* of the measuring units 10A, 10B, 11C . . . . Next, the controller 69 causes the sheet supply portion 78 to rotate the sheet holding portion 76 a predetermined angle (predetermined amount) in the direction where the cover sheet 77 is supplied. With this operation, the openings 13*a* of the measuring units 10A, 10B, 10C . . . of the measuring-unit array 68 are covered with the leading end portion of the cover sheet 77. If the openings 13*a* are covered with the cover sheet 77, the liquid-sample holding portions 13*b* of the measuring units 10A, 10B, 10C . . . are hermetically sealed and the amount of liquid that evaporates per hour becomes 2% or less. Because of this, the samples 15 hardly evaporate during measurement.

As described above, with the openings 13*a* of the measuring units 10A, 10B, 10C . . . covered with the leading end portion of the cover sheet 77, the state of ATR is measured. Because the measuring operation in the surface plasmon resonance sensor units 98A, 98B, 98C . . . is nearly the same as that of the first embodiment, a description of the measuring operation is omitted. After the measurement, the controller 69 causes the sheet supply portion 78 to rotate the sheet holding portion 76 a predetermined angle (predetermined amount) in the reverse direction. Because of this, the cover sheet 77 is wound on the sheet holding portion 76.

In the fourth embodiment shown in FIGS. 14 to 16, the liquid samples 15 are first supplied to the liquid-sample holding portions 13*b*, then the openings 13*a* of the measuring units 10A, 10B, 10C . . . are covered with the leading end portion of the cover sheet 77, and the liquid-sample holding portions 13*b* of the measuring units 10A, 10B, 10C . . . are hermetically sealed and the amount of liquid that evaporates per hour becomes 2% or less. As a result, the samples 15 hardly evaporate during measurement, the concentration of each liquid sample 15 is kept constant, and the generation of evaporation heat can be prevented. Thus, the measurement accuracy of the state of ATR is enhanced. Note that it is further desirable that the amount of liquid that evaporates per hour is 0.5% or less. In addition, the cover sheet 77 can be placed more easily on the openings 13*a*, because there is no need to perform precise alignment when placing the cover sheet 77 on the openings 13*a*.

Furthermore, since a single cover sheet 77 is employed to cover a plurality of liquid-sample holding portions 13*b*, it can be placed on the openings 13*a* of the measuring units 10A, 10B, 10C . . . by a single operation and therefore the cover sheet 77 can be efficiently placed.

Figure 17:
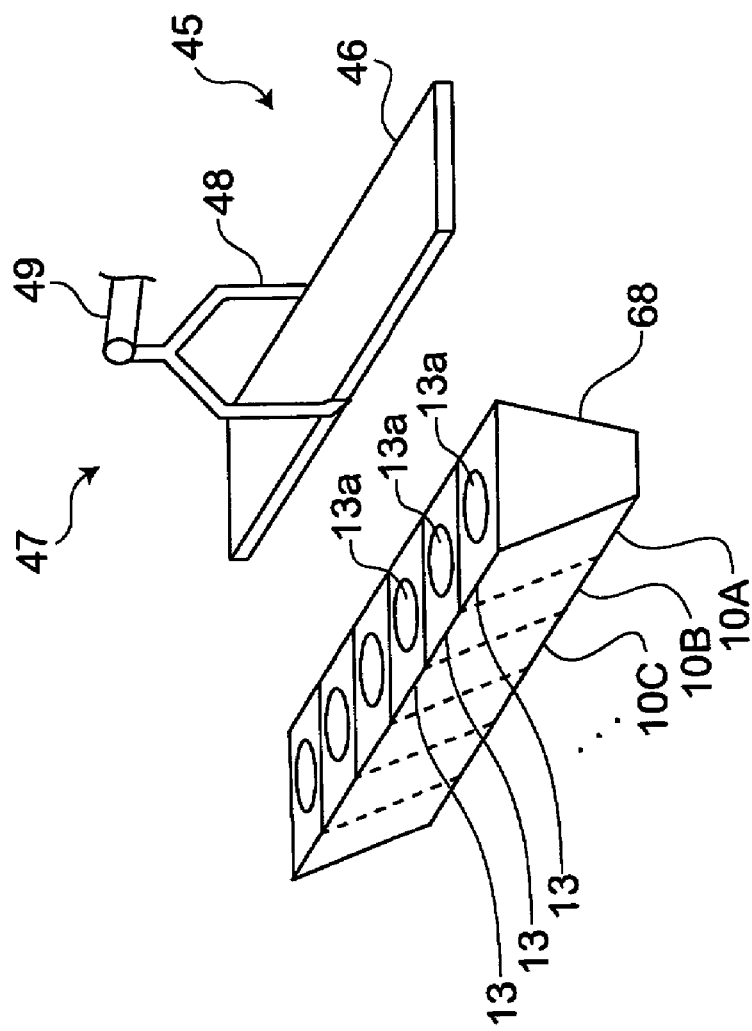
FIG. 17 is a perspective view of the lid supply mechanism employed in the surface plasmon resonance sensor shown in FIG. 14.

As a first modification of the fourth embodiment, there is a surface plasmon resonance sensor having a lid supply mechanism 45 instead of having the sheet supply mechanism 75, as shown in FIG. 17. The lid supply mechanism 45 is equipped with a lid 46 and a lid supply portion 47 for placing the lid 46 on the openings 13*a* of the liquid-sample holding portions 13*b* of the measuring unit array 68. The lid supply portion 47 is constructed of a holding portion 48 for holding the lid 46 and means 49 for moving the holding portion 48. The controller 69 controls operation of the lid supply portion 47, and causes the lid supply portion 47 to place the lid 46 on the openings 13*a* of the liquid-sample holding portions 13*b* of the measuring unit array 68 as needed. The lid 46 can employ a flat plate; a plate with protruding portions in the form of a truncated cone slightly smaller in diameter than the opening 13*a* of the liquid-sample holding portion 13*b* at positions corresponding to the openings 13*a* of the liquid-sample holding portions 13*b*; a plate with protruding portions in the form of a bowl slightly greater in diameter than the opening 13*a* of the liquid-sample holding portion 13*b* at positions corresponding to the openings 13*a* of the liquid-sample holding portions 13*b*; etc. If soft resin or rubber is employed as the material of the above-mentioned lids, the close contact property between the openings 13*a* and the lid is enhanced and therefore evaporation of the liquid samples 15 can be further prevented. In addition, if a sealant, such as oil, etc., is employed between the upper portion of the measuring unit array 68 and the lid, the close contact property therebetween is further enhanced.

Figure 18:
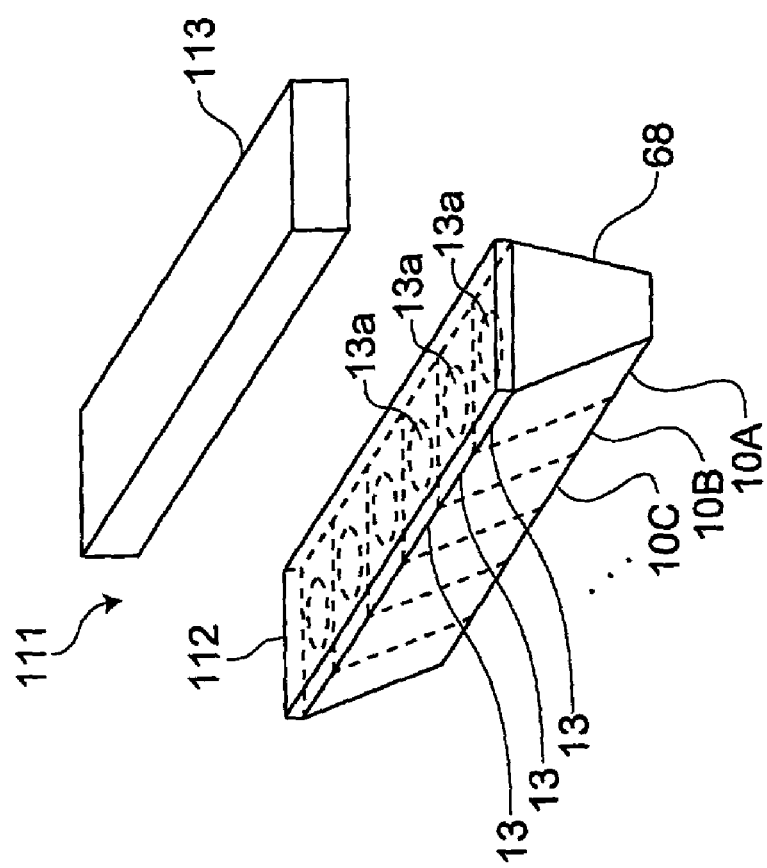
FIG. 18 is a perspective view of the resin-sheet supply mechanism employed in the surface plasmon resonance sensor shown in FIG. 14.

As a second modification of the fourth embodiment, there is a surface plasmon resonance sensor having a resin sheet supply mechanism 111 instead of having the sheet supply mechanism 75, as shown in FIG. 18. The resin sheet supply mechanism 111 is equipped with a resin sheet 112 and a sheet bonding portion 113 for bonding the resin sheet 112 to the top portion of the measuring unit array 68 by thermo compression bonding. If such a resin sheet 112 is employed as the lid, there is no possibility of the lid being disconnected from the measuring unit array 68 when the measuring unit array 68 is moved. Note that because the resin sheet 112 is bonded to the top portion of the measuring unit array 68 by thermo compression bonding, it can be easily removed when it becomes unnecessary.

Figure 19:
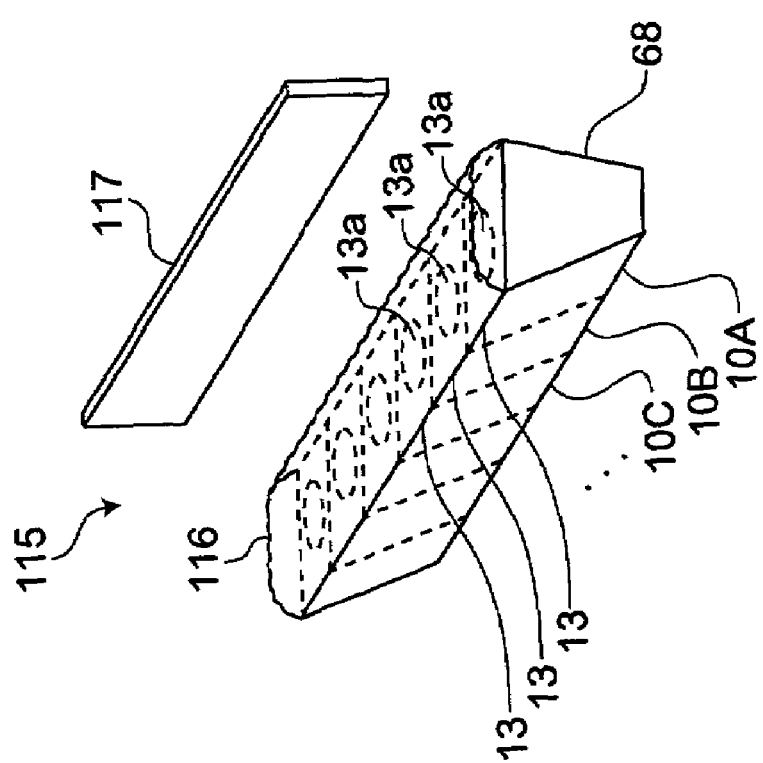
FIG. 19 is a perspective view of the viscous-fluid supply mechanism employed in the surface plasmon resonance sensor shown in FIG. 14.

As a third modification of the fourth embodiment, there is a surface plasmon resonance sensor having a viscous fluid supply mechanism 115 instead of having the sheet supply mechanism 75, as shown in FIG. 19. The viscous fluid supply mechanism 115 is equipped with a viscous fluid 116 such as grease, etc., and a viscous fluid supply portion 117 for supplying the viscous fluid 116 to the top portion of the measuring unit array 68. If such a viscous fluid 116 is employed as the lid, the lid can be placed on the measuring unit array 68 before the supply of the liquid samples 15, because the liquid samples 15 can be supplied to the liquid-sample holding portions 13*b* of the measuring unit array 68 by inserting the pipette of the liquid-sample supply mechanism into the viscous fluid 116.

Figure 20:
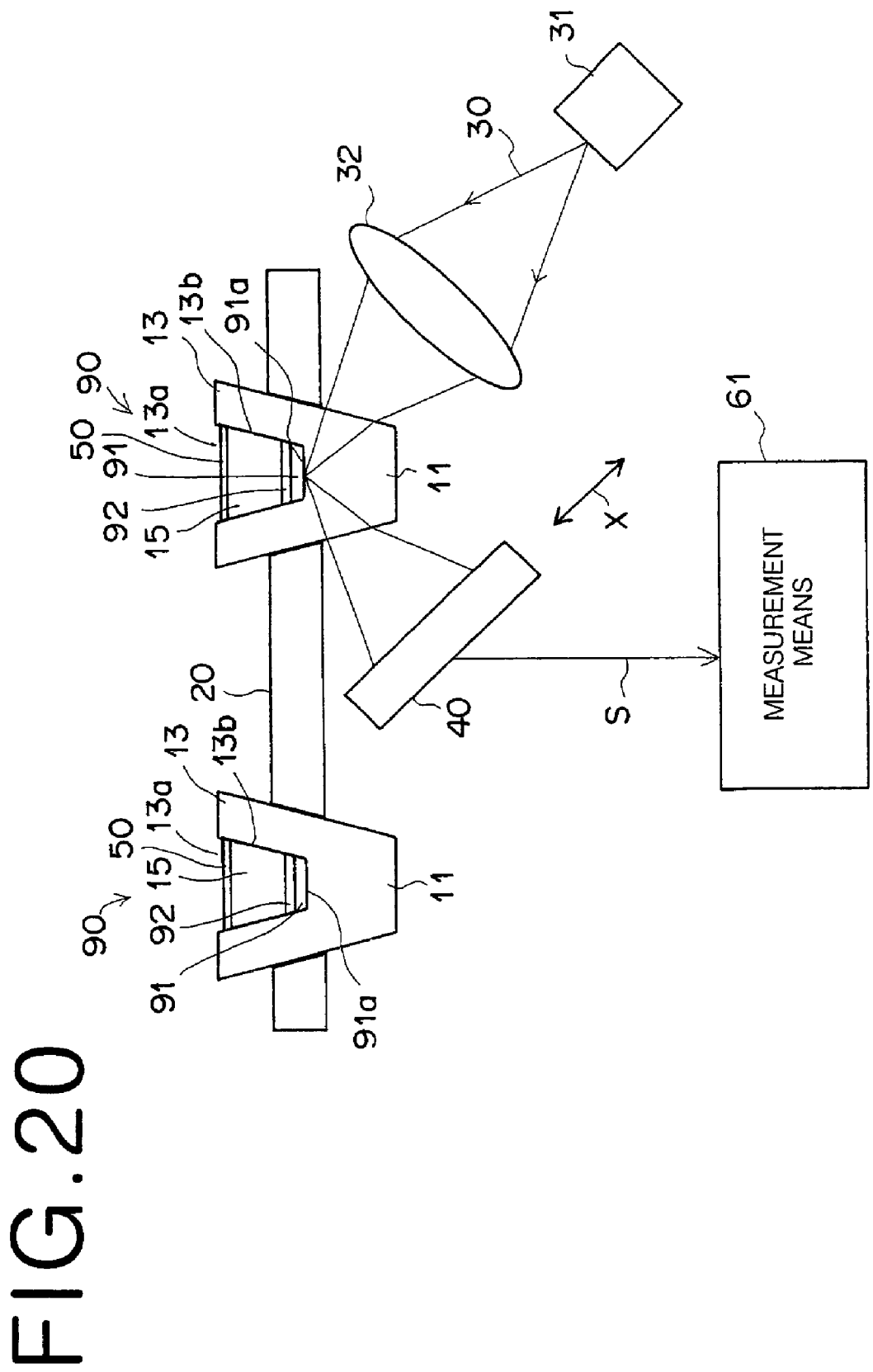
FIG. 20 is a part-sectional side view showing a leaky mode sensor constructed according to a fifth embodiment of the present invention.

FIG. 20 shows a leaky mode sensor utilizes ATR, constructed according to a fifth embodiment of the present invention. Since the fifth embodiment is nearly the same as the first embodiment, only a reference numeral (90) for a different part is shown in FIG. 1. Note in FIG. 20 that the same reference numerals are applied to the same parts as those in FIG. 2, and that a description of the same parts will not be given unless particularly necessary.

The leaky mode sensor of the fifth embodiment similarly employs a measuring unit 90 which functions as a measuring chip. The top surface of the dielectric block 11 of the measuring unit 90 has a cladding layer 91 on which an optical waveguide layer 92 is formed.

The dielectric block 11 is formed, for example, from synthetic resin, or optical glass such as BK7, etc. The cladding layer 91 is formed into the shape of a thin film by employing a dielectric or metal (such as gold, etc.) lower in refractive index than the dielectric block 11. The optical waveguide layer 92 is also formed into a thin film by employing a dielectric, which is higher in refractive index than the cladding layer 91, such as polymethylmethacrylate (PMMA). The cladding layer 91 is, for example, 36.5 nm in thickness when it is formed from a thin gold film. The optical waveguide layer 92 is, for example, about 700 nm in thickness when it is formed from PMMA.

In the leaky mode sensor of the fifth embodiment, if a light beam 30 emitted from a laser light source 31 strikes the cladding layer 91 through the dielectric block 11 at incidence angles greater than a critical angle at which total internal reflection (TIR) occurs, the light beam 30 is totally reflected at the interface 91*a* between the dielectric block 11 and the cladding layer 91. However, the light with a specific wave number, incident on the optical waveguide layer 92 through the cladding layer 91 at a specific incidence angle, propagates through the optical waveguide layer 92 in a waveguide mode. If the waveguide mode is excited in this manner, most of the incident light is confined within the optical waveguide layer 92, and consequently, ATR occurs in which the intensity of the light totally reflected at the interface 91*a* drops sharply.

The wave number of the light propagating through the optical waveguide layer 92 depends upon the refractive index of a liquid sample 15 on the optical wave guide layer 92. Therefore, the refractive index of the liquid sample 15 can be measured by finding the above-mentioned specific incidence angle $\theta_{sp}$ at which ATR takes place.

In the fifth embodiment, as with the aforementioned embodiments, a liquid sample 15 is first supplied to a liquid-sample holding portion 13b and then oil 50 is supplied to the liquid-sample holding portion 13b. The surface of the liquid sample 15 is covered with the oil. Because of this, evaporation of the liquid sample 15 is prevented and accuracy of measurement is enhanced. Particularly, in the case of measuring a temporal change in the aforementioned specific incidence angle $\theta_{sp}$ (at which ATR occurs), evaporation of the liquid sample 15 is prevented even if measurements are made for extensive periods of time. Thus, the accuracy of the measurement of a temporal change in the state of ATR is enhanced. In the fifth embodiment, the same modifications as those in the first embodiment are applicable and the same advantages can be obtained. In addition, the fifth embodiment can be constructed the same as the second embodiment and the third embodiment and obtain the same advantages. Furthermore, the fifth embodiment can be constructed as a sensor that employs a measuring unit array equipped with a plurality of liquid-sample holding portions, as with the fourth embodiment.

Figure 21:
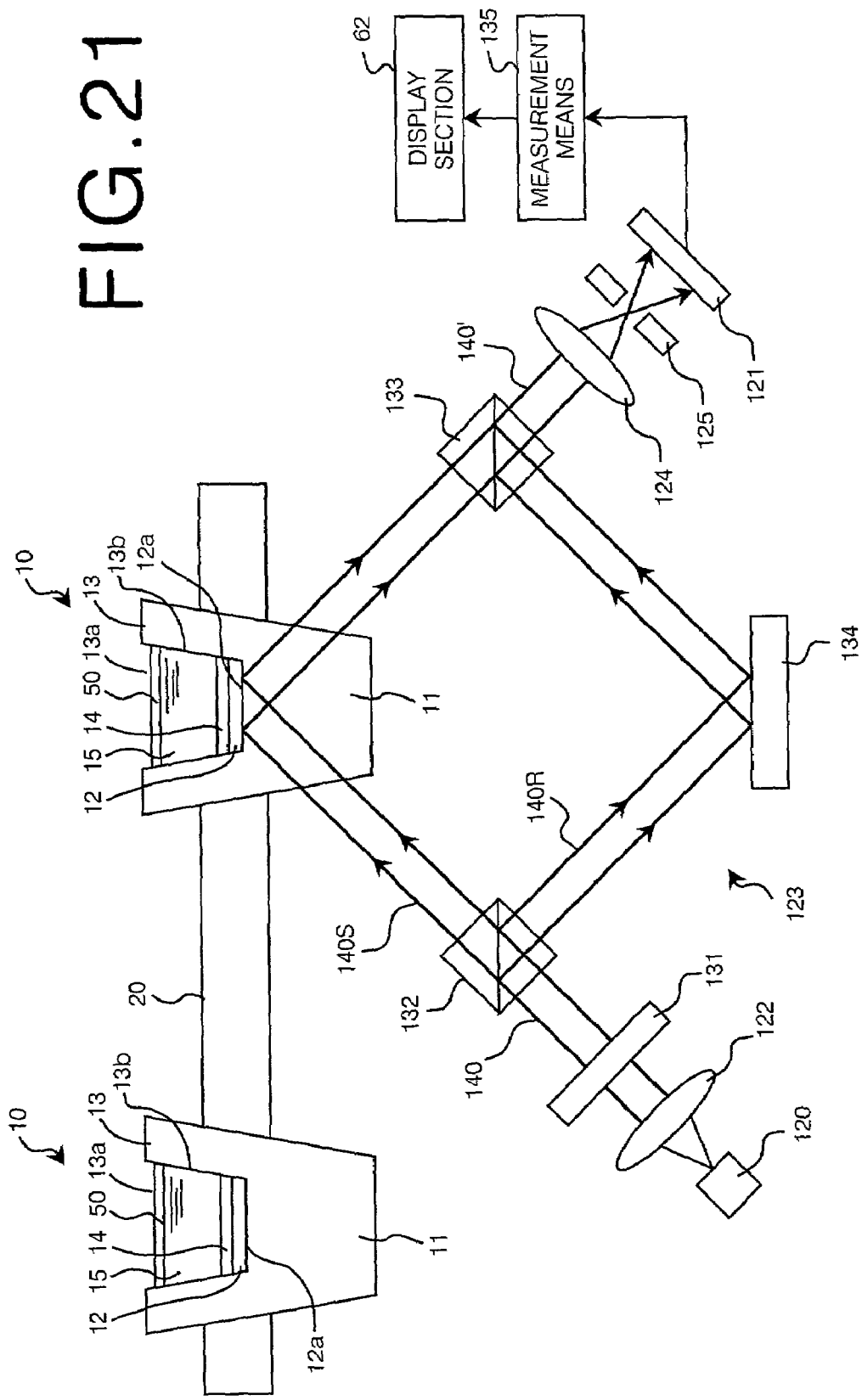
FIG. 21 is a part-sectional side view showing a leaky mode sensor constructed according to a sixth embodiment of the present invention.

FIG. 21 shows a surface plasmon resonance sensor constructed according to a sixth embodiment of the present invention. The surface plasmon resonance sensor of the sixth embodiment is the same in construction as the first embodiment shown in FIG. 1. In the sixth embodiment, the manner in which samples are measured is different from that of the first embodiment. In addition, in the sixth embodiment, a sensing substance 14 is fixed on a metal film 12, and it is judged whether or not a target substance contained in a liquid sample 15 is a specific substance that bonds to the sensing substance 14.

As shown in FIG. 21, the surface plasmon resonance sensor of the sixth embodiment is equipped with a laser light source 120 and a charge-coupled device (CCD) 121, which are disposed at measuring positions. The surface plasmon resonance sensor is further equipped with a collimator lens 122, an optical interference system 123, a condenser lens 124, and an aperture plate 125, which are disposed between the laser light source 120 and the CCD 121.

The optical interference system 123 is constructed of a polarizing filter 131, a first half mirror 132, a second half mirror 133, and a third mirror 134. The CCD 121 is connected to measurement means 135, which is in turn connected to a display section 62.

A description will hereinafter be given of how measurements are made by the surface plasmon resonance sensor of the sixth embodiment. The laser light source 121 is driven and a light beam 140 is divergently emitted. The light beam 140 is collimated by the collimator lens 122 and enters the polarizing filter 131. The light beam 140 is transmitted through the polarizing filter 131 so that it enters an interface 12a as a p-polarized light beam. The light beam 140 from the polarizing filter 131 is split into a reference light beam 14CR and a light beam 140S by the first half mirror 132. The light beam 140S strikes the interface 12a. The light beam 140S totally reflected at the interface 12a, and the reference light beam 140R reflected at the mirror 134, are synthesized into a light beam 140' by the second half mirror 133. The synthesized light beam 140' is condensed by the condenser lens 124. The light beam 140' is passed through the aperture plate 125 and detected by the CCD 121. When it arises, the light beam 140' detected by the CCD 121 produces an interference fringe according to the state of the interference between the light beam 140S and the reference light beam 140R.

In the sixth embodiment, whether or not the sensing substance 14 fixed on the surface of the metal film 12 bonds to a target substance in the liquid sample 15, that is, whether or not the target substance is a specific substance which bonds to the sensing substance 14, can be judged by measuring the liquid sample 15 continuously after dropping of the liquid sample 15, and then detecting a change in the interference fringe detected by the CCD 121.

That is, since the refractive index of the sensing substance 14 changes according to the bonded state between the target substance in the liquid sample 15 and the sensing substance 14, the state of interference fringe changes when the light beam 140S and the reference light beam 140R are synthesized by the half mirror 133. Therefore, a bonding reaction can be detected according to a change in the interference fringe. The measurement means 135 detects the above-mentioned reaction, based on the aforementioned principle. The result of detection is displayed on the display section 62.

To perform such a judgment, there is a need to measure one measuring unit 10 a plurality of times. In this case, if the measuring unit 10 remains supported by the turntable 20 after a first measurement, the measuring unit 10 can be measured again by rotation of the turntable 20. When one measuring unit 10 is thus measured for an extensive period of time, there is a possibility that the concentration of the liquid sample 15 will change due to evaporation of the liquid sample 10. However, since the surface of the liquid sample 15 is covered with oil, evaporation of the liquid sample 15 is prevented and the accuracy of the measurement of a temporal change in the state of ATR is enhanced.

In the sixth embodiment, the same modifications as those in the first embodiment are applicable and the same advantages can be obtained. In addition, the sixth embodiment can be constructed the same as the second embodiment and the third embodiment and obtain the same advantages. Furthermore, the sixth embodiment can be constructed as a sensor that employs a measuring unit array equipped with a plurality of liquid-sample holding portions, as with the fourth embodiment.

Finally, although the present invention has been described with reference to the preferred embodiments and modifications, the invention is not to be limited to the details given herein, but may be modified within the scope of the invention hereinafter claimed.

What is claimed is:

1. A sensor utilizing attenuated total reflection, comprising:
   a light source for emitting a light beam;
   a measuring chip comprising
   a dielectric block transparent to said light beam, a thin film layer formed on the top surface of said dielectric block, and one or a plurality of liquid-sample holding portions for holding a liquid sample on said thin film layer;
   an optical system for making said light beam enter said dielectric block at various angles of incidence so that a total internal reflection condition is satisfied at an interface between said dielectric block and said thin film layer;
   photodetection means for detecting intensity of said light beam totally reflected at said interface; and measurement means for measuring a state of attenuated total reflection, based on the result of detection obtained by said photodetection means;

wherein the liquid-sample holding portion of said measuring chip has an opening at its top surface;

and wherein said sensor further comprises a lid-means supply means for placing a lid means on said opening to prevent evaporation of said liquid sample.

2. The sensor as set forth in claim 1, wherein a sensing substance that bonds to said liquid sample is placed on said thin film layer, and said measurement means measures a temporal change in the state of attenuated total reflection, based on a plurality of results of detection obtained at predetermined intervals by said photodetection means.

3. The sensor as set forth in claim 1, wherein said lid means is oil, and said lid-means supply means supplies said oil to said opening.

4. The sensor as set forth in claim 2, wherein said lid means is oil, and said lid-means supply means supplies said oil to said opening.

5. The sensor as set forth in claim 1, wherein said lid means is a lid, and said lid-means supply means places said lid on said opening.

6. The sensor as set forth in claim 2, wherein said lid means is a lid, and said lid-means supply means places said lid on said opening.

7. The sensor as set forth in claim 3, wherein said lid means is a lid, and said lid-means supply means places said lid on said opening.

8. The sensor as set forth in claim 4, wherein said lid has a hole smaller than said opening.

9. The sensor as set forth in claim 4, wherein said lid is formed into the shape of a reed screen capable of expansion and contraction.

10. The sensor as set forth in claim 4, wherein said lid is formed into a sheet shape.

11. The sensor as set forth in any one of claims 1 through 10, wherein, in said liquid-sample holding portion with said lid means placed on said opening, the amount of liquid that evaporates per hour becomes 2% or less.

12. A measuring chip assembly comprising:
a measuring chip comprising
a dielectric block transparent to a light beam, a thin film layer formed on a top surface of said dielectric block, and one or a plurality of liquid-sample holding portions for holding a liquid sample on said thin film layer; and
a lid provided on an opening of said measuring chip,
wherein said measuring chip is adapted to a sensor utilizing attenuated total reflection, said sensor comprising:
a light source for emitting said light beam;
an optical system for making said light beam enter said dielectric block at various angles of incidence so that a total internal reflection condition is satisfied at an interface between said dielectric block and said thin film layer;
photodetection means for detecting intensity of said light beam totally reflected at said interface;
measurement means for measuring a state of attenuated total reflection, based on the result of detection obtained by said photodetection means; and
a lid-means supply means for placing said lid on said opening to prevent evaporation of said liquid sample.

13. A measuring chip assembly as set forth in claim 12, wherein said lid has a hole smaller than said opening.

14. A measuring chip assembly comprising:
a measuring chip, which is employed in a sensor utilizing attenuated total reflection, comprising
a dielectric block transparent to a light beam, a thin film layer formed on a top surface of said dielectric block, and one or a plurality of liquid-sample holding portions for holding a liquid sample on said thin film layer; and
a lid provided on an opening of said measuring chip,
wherein said lid is formed into the shape of a reed screen capable of expansion and contraction.

15. The measuring chip assembly as set forth in claim 12, wherein said lid is formed into a sheet shape.

16. A measuring chip assembly as set forth in claim 12, wherein, in said liquid-sample holding portion with said lid placed on said opening, the amount of liquid that evaporates per hour becomes 2% or less.

17. The measuring chip assembly as set forth in claim 13, wherein, in said liquid-sample holding portion with said lid placed on said opening, the amount of liquid that evaporates per hour becomes 2% or less.

18. The measuring chip assembly as set forth in claim 14, wherein, in said liquid-sample holding portion with said lid placed on said opening, the amount of liquid that evaporates per hour becomes 2% or less.

19. The measuring chip assembly as set forth in claim 16, wherein said lid is formed into a sheet shape.

* * * * *